(12) United States Patent
Thuillier et al.

(10) Patent No.: US 7,169,913 B2
(45) Date of Patent: Jan. 30, 2007

(54) ENGINEERED SECRETED ALKALINE PHOSPHATASE (SEAP) REPORTER GENES AND POLYPEPTIDES

(75) Inventors: Vincent Thuillier, Bures sur Yvette (FR); Manping Wang, Fremont, CA (US); Cecile Orsini, Paris (FR)

(73) Assignee: Aventis Pharma SA, Antony (FR)

( * ) Notice: Subject to any disclaimer, the term of this patent is extended or adjusted under 35 U.S.C. 154(b) by 453 days.

(21) Appl. No.: 10/155,229

(22) Filed: May 28, 2002

(65) Prior Publication Data

US 2003/0104422 A1 Jun. 5, 2003

Related U.S. Application Data

(60) Provisional application No. 60/293,186, filed on May 25, 2001.

(51) Int. Cl.
C07H 21/04 (2006.01)
(52) U.S. Cl. .................................. 536/23.2; 435/252.3
(58) Field of Classification Search ................ 536/23.1; 435/252.3, 325; 535/23.2
See application file for complete search history.

(56) References Cited

OTHER PUBLICATIONS

Mullins et al. (1996) J. Clin. Invest. vol. 98, pp. 1557-1560.*
Mullins et al. (1993) Hypertension vol. 22, pp. 630-633.*
Cameron (1997) Molec. Biotech. vol. 7, pp. 253-265.*
Kappel et al. (1992) Current Opinion in Biotechnology, vol. 3, pp. 548-553.*
Berger, et al., Secreted placental alkaline phosphatase: a powerful new quantitative indicator of gene expression in eukaryotic cells, Gene 66, 1-10 (1988).
Nilsson, et al., An in vivo mouse reporter gene (human secreted alkaline phosphatase) model to monitor ovarian tumor growth and rsponse to therapeutics, Cancer Chemotherapy and Pharmacology 49, 93-100 (2001).
Mir, et al., High-efficiency gene transfer into skeletal muscle mediated by electric pulses, PNAS 96, 4262-7, (1999).
Urlinger, et al., Exploring the sequence space for tetracycline-dependent transcriptional activators: Novel mutations yield expanded range and sensitivity, PNAS 97, 7963-68 (2000).
Manes, et al., Genomic Structure and Comparison of Mouse Tissue-Specific Alkaline Phosphatase Genes, Genomics 8, 541-554 (1990).

Hahnel, et al., Two alkaline phosphatase genes are expressed during early development in the mouse embryo, Development 110, 555-564 (1990).
Bao, et al., Use of a Surrogate Marker (Human Secreted Alkaline Phosphatase) to Monitor in Vivo Tumor Growth and Anticancer Drug Efficacy in Ovarian Cancer Xenografts, Gynecologic Oncology 78, 373-379 (2000).
Narisawa, et al., Embryonic alkaline phosphatase is expressed at M-phase in the spermatogenic lineage of the mouse, Development 116, 159-165 (1992).
Soubrier, et al., pCOR: a new design of plasmid vectors for nonviral gene therapy, Gene Therapy 6, 1482-1488 (1999).
Burbridge, et al., Biological and pharmacological characterisation of three models of human ovarian carcinoma established in nude mice: Use of the CA125 tumour marker to predict antitumour activity, International Journal of Oncology 15, 1155-1162 (1999).
Abruzzese, et al., Ligand-Dependent Regulation of Plasmid-Based Transgene Expression in Vivo, Human Gene Therapy 10, 1499-1507 (1999).
Mujtaba, et al., Stable Expression of the Alkaline Phosphatase Marker Gene by Neural Cells is Culture and after Transplanataion into the CNS Using Cells Derived from a Transgenic Rat, Experimental Neurology 174, 48-57 (2002).
Bettan, et al., High-Level Protein Secretion into Blood Circulation after Electric Pulse-Mediated Gene Transfer into Skeletal Muscle, Molecular Therapy 2, 204-210 (2000).
Latta-Mahieu, et al., Immunogenicity of the Tetracycline-Dependent Transcription Factor in Monkeys and its Impact on Reporter Gene Expression, Molecular Therapy 3, S398 (2001) (Abstract).
Rubinchik, et al., A Novel Adenovirus Vector Incorporating a Complex Tet Regulation System Delivers Tightly Regulated Transgene Expression With a Range of Over Three Orders of Magniture, Molecular Therapy 3, S398 (2001) (Abstract).
Excerpt from Applied Biosystems, Phospha-Light Secreted Alkaline Phosphatase Reporter Gene Assay System (2002).
Excerpt from Turner BioSystems Applications Note, A TD-20/20 Luminometer method for Secreted Embryonic Alkaline Phosphatase (SEAP), (Mar. 20, 2002).
Excerpt from Great EscAPe SEAP User Manual, CLONTECH Laboratories, Inc., Protocol #PT3057-1, Version #PR98443.
Excerpt from CLONTECHniques, Reporter Systems & Detection Kits, Oct. 2001.

* cited by examiner

*Primary Examiner*—Jon Angell
(74) *Attorney, Agent, or Firm*—Wiley Rein & Fielding LLP

(57) ABSTRACT

The invention provides a novel reporter gene (mSEAP) capable of being expressed in a mammal for extended periods of time. Nucleic acids encoding the reporter gene, cells and vectors comprising the nucleic acids, and methods of using the reporter gene to identify expression vectors and screen for drug compounds in an animal are also disclosed.

21 Claims, 10 Drawing Sheets

Figure 1B

```
                                    310         320         330         340         350         360
SEQ ID NO: 14   hSEAP(300)  (301)301 TLDPSLMEMTEAALRTLSRNPRGFELFVEGGRIDHGHHESRAYRALTETLMFDDAIERAG
SEQ ID NO: 13   mEAP(301)           AQDPSLAEMTEVAVRMLSRNPKGFYLFVEGGRIDHGHHETVAYRALTEAVMFDSAVDKAD
SEQ ID NO: 2    mSEAP(301)          AQDPSLAEMTEVAVRMLSRNPKGFYLFVEGGRIDHGHHETVAYRALTEAVMFDSAVDKAD
SEQ ID NO: 2    Consensus(301)      AQDPSLAEMTEVAVRMLSRNPKGFYLFVEGGRIDHGHHETVAYRALTEAVMFDSAVDKAD 370         380         390         400         410         420
                hSEAP(360)  (361)361 QLTSEEDTLSLVTADHSHVFSFGGYPLRGSSIFGLAPGKARDRKAYTVELYGNGPGYVLK
                mEAP(361)           KLTSEQDTMILVTADHSHVFSFGGYTQRGASIFGLAPFKAEDGKSFTSILYGNGPGYKLH
                mSEAP(361)          KLTSEQDTMILVTADHSHVFSFGGYTQRGASIFGLAPFKAEDGKSFTSILYGNGPGYKLH
                Consensus(361)      KLTSEQDTMILVTADHSHVFSFGGYTQRGASIFGLAPFKAEDGKSFTSILYGNGPGYKLH 430         440         450         460         470         480
                hSEAP(420)  (421)421 DGARPDVTESESGSPEYRQQSAVPLDEETHAGEDVAMFARGPQAHLVHGVQEQTEIAHVM
                mEAP(421)           NGARADVTEEESSNPTYQQQACVPLSSETHSGEDVAIFARGPQAHLVHGVQEQNYIAHVM
                mSEAP(421)          NGARADVTEEESSNPTYQQQAAVPLSSETHSGEDVAIFARGPQAHLVHGVQEQNYIAHVM
                Consensus(421)      NGARADVTEEESSNPTYQQQAAVPLSSETHSGEDVAIFARGPQAHLVHGVQEQNYIAHVM 490         500         510         520         530
                hSEAP(480)  (481)    AFAACLEPYTACDLAPPAGTTDAAHPG----------------------
                mEAP(481)           AFAACLEPYTDCGLASPAGQSSAVSPGYMSTLLCLLAGKMLMLMAAAEP-
                mSEAP(481)          AFAACLEPYTDCGLASPAGQSSAVSPG----------------------
                Consensus(481)      AFAACLEPYTDCGLASPAGQSSAVSPG
```

Figure 7

SEQ ID NO: 2   mSEAP- substitution sites (1)    MWGACLLLLGLSLQLCPSIIPVEEENPAFWNRKAAEALDAAKKLKPIQTSAKNLVILMGD

(61)   GMGVSTVTATRILKGQQQGHLGPETQLAMDRFPHMALSKTYNTDKQIPDSAGTGTAFLCG (121)  VKTNMKVIGLSAAAARFNQCNTTWGNEVVSVMHRAKKAGKSVGVVTTTSVQHASPAGTYAH (181)  TVNRGWYSDAQMPASALQDGCKDISTQLISNMDIDVILGGGRKFMFPKGTPDQEYPTDTK (241)  QAGTRLDGRNLVQEWLAKHQGARYVWNRSELIQASLNRSVTHLMGLFEPNDMKYEIHRDP (301)  AQDPSLAEMTEVAVRMLSRNPKGFYLFVEGGRIDHGHHETVAYRALTEAVMFDSAVDKAD (361)  KLTSEQDTMILVTADHSHVFSFGGYTQRGASIFGLAPFKAEDGKSFTSILYGNGPGYKLH (421)  NGARADVTEEESSNPTYQQQAAVPLSSETHSGEDVAIFARGPQAHLVHGVQEQNYIAHVM (481)  AFAACLEPYTDCGLASPAGQSSAVSPG

SEQUENCE LISTING

<160> NUMBER OF SEQ ID NOS: 13

<210> SEQ ID NO 1
<211> LENGTH: 488
<212> TYPE: PRT
<213> ORGANISM: Artificial
<220> FEATURE:
<223> OTHER INFORMATION: Recombinant AP-activity polypeptide

<400> SEQUENCE: 1

Ile Pro Val Glu Glu Glu Asn Pro Ala Phe Trp Asn Arg Lys Ala Ala
1               5                   10                  15

Glu Ala Leu Asp Ala Ala Lys Lys Leu Lys Pro Ile Gln Thr Ser Ala
            20                  25                  30

Lys Asn Leu Val Ile Leu Met Gly Asp Gly Met Gly Val Ser Thr Val
        35                  40                  45

Thr Ala Thr Arg Ile Leu Lys Gly Gln Gln Gln Gly His Leu Gly Pro
    50                  55                  60

Glu Thr Gln Leu Ala Met Asp Arg Phe Pro His Met Ala Leu Ser Lys
65                  70                  75                  80

Thr Tyr Asn Thr Asp Lys Gln Ile Pro Asp Ser Ala Gly Thr Gly Thr
                85                  90                  95

Ala Phe Leu Cys Gly Val Lys Thr Asn Met Lys Val Ile Gly Leu Ser
            100                 105                 110

Ala Ala Ala Arg Phe Asn Gln Cys Asn Thr Thr Trp Gly Asn Glu Val
        115                 120                 125

-continued

```
Val Ser Val Met His Arg Ala Lys Lys Ala Gly Lys Ser Gly Val
    130                 135                 140
Val Thr Thr Thr Ser Val Gln His Ala Ser Pro Ala Gly Thr Tyr Ala
145                 150                 155                 160
His Thr Val Asn Arg Gly Trp Tyr Ser Asp Ala Gln Met Pro Ala Ser
                165                 170                 175
Ala Leu Gln Asp Gly Cys Lys Asp Ile Ser Thr Gln Leu Ile Ser Asn
            180                 185                 190
Met Asp Ile Asp Val Ile Leu Gly Gly Gly Arg Lys Phe Met Phe Pro
        195                 200                 205
Lys Gly Thr Pro Asp Gln Glu Tyr Pro Thr Asp Thr Lys Gln Ala Gly
    210                 215                 220
Thr Arg Leu Asp Gly Arg Asn Leu Val Gln Glu Trp Leu Ala Lys His
225                 230                 235                 240
Gln Gly Ala Arg Tyr Val Trp Asn Arg Ser Glu Leu Ile Gln Ala Ser
                245                 250                 255
Leu Asn Arg Ser Val Thr His Leu Met Gly Leu Phe Glu Pro Asn Asp
            260                 265                 270
Met Lys Tyr Glu Ile His Arg Asp Pro Ala Gln Asp Pro Ser Leu Ala
        275                 280                 285
Glu Met Thr Glu Val Ala Val Arg Met Leu Ser Arg Asn Pro Lys Gly
    290                 295                 300
Phe Tyr Leu Phe Val Glu Gly Gly Arg Ile Asp His Gly His His Glu
305                 310                 315                 320
Thr Val Ala Tyr Arg Ala Leu Thr Glu Ala Val Met Phe Asp Ser Ala
                325                 330                 335
Val Asp Lys Ala Asp Lys Leu Thr Ser Glu Gln Asp Thr Met Ile Leu
            340                 345                 350
Val Thr Ala Asp His Ser His Val Phe Ser Phe Gly Gly Tyr Thr Gln
        355                 360                 365
Arg Gly Ala Ser Ile Phe Gly Leu Ala Pro Phe Lys Ala Glu Asp Gly
    370                 375                 380
Lys Ser Phe Thr Ser Ile Leu Tyr Gly Asn Gly Pro Gly Tyr Lys Leu
385                 390                 395                 400
His Asn Gly Ala Arg Ala Asp Val Thr Glu Glu Ser Ser Asn Pro
                405                 410                 415
Thr Tyr Gln Gln Gln Ala Ala Val Pro Leu Ser Ser Glu Thr His Ser
                420                 425                 430
Gly Glu Asp Val Ala Ile Phe Ala Arg Gly Pro Gln Ala His Leu Val
            435                 440                 445
His Gly Val Gln Glu Gln Asn Tyr Ile Ala His Val Met Ala Phe Ala
    450                 455                 460
Ala Cys Leu Glu Pro Tyr Thr Asp Cys Gly Leu Ala Ser Pro Ala Gly
465                 470                 475                 480
Gln Ser Ser Ala Val Ser Pro Gly
                485
```

```
<210> SEQ ID NO 2
<211> LENGTH: 507
<212> TYPE: PRT
<213> ORGANISM: Artificial
<220> FEATURE:
<223> OTHER INFORMATION: mSEAP

<400> SEQUENCE: 2
```

-continued

```
Met Trp Gly Ala Cys Leu Leu Leu Gly Leu Ser Leu Gln Val Cys
1               5                   10                  15

Pro Ser Val Ile Pro Val Glu Glu Asn Pro Ala Phe Trp Asn Arg
                20              25                  30

Lys Ala Ala Glu Ala Leu Asp Ala Ala Lys Leu Lys Pro Ile Gln
            35              40              45

Thr Ser Ala Lys Asn Leu Val Ile Leu Met Gly Asp Gly Met Gly Val
        50                  55              60

Ser Thr Val Thr Ala Thr Arg Ile Leu Lys Gly Gln Gln Gln Gly His
65              70                  75                  80

Leu Gly Pro Glu Thr Gln Leu Ala Met Asp Arg Phe Pro His Met Ala
                85                  90                  95

Leu Ser Lys Thr Tyr Asn Thr Asp Lys Gln Ile Pro Asp Ser Ala Gly
            100             105             110

Thr Gly Thr Ala Phe Leu Cys Gly Val Lys Thr Asn Met Lys Val Ile
        115             120             125

Gly Leu Ser Ala Ala Ala Arg Phe Asn Gln Cys Asn Thr Thr Trp Gly
        130             135             140

Asn Glu Val Val Ser Val Met His Arg Ala Lys Lys Ala Gly Lys Ser
145             150             155             160

Val Gly Val Val Thr Thr Thr Ser Val Gln His Ala Ser Pro Ala Gly
            165             170             175

Thr Tyr Ala His Thr Val Asn Arg Gly Trp Tyr Ser Asp Ala Gln Met
            180             185             190

Pro Ala Ser Ala Leu Gln Asp Gly Cys Lys Asp Ile Ser Thr Gln Leu
        195             200             205

Ile Ser Asn Met Asp Ile Asp Val Ile Leu Gly Gly Gly Arg Lys Phe
210             215             220

Met Phe Pro Lys Gly Thr Pro Asp Gln Glu Tyr Pro Thr Asp Thr Lys
225             230             235             240

Gln Ala Gly Thr Arg Leu Asp Gly Arg Asn Leu Val Gln Glu Trp Leu
            245             250             255

Ala Lys His Gln Gly Ala Arg Tyr Val Trp Asn Arg Ser Glu Leu Ile
            260             265             270

Gln Ala Ser Leu Asn Arg Ser Val Thr His Leu Met Gly Leu Phe Glu
        275             280             285

Pro Asn Asp Met Lys Tyr Glu Ile His Arg Asp Pro Ala Gln Asp Pro
290             295             300

Ser Leu Ala Glu Met Thr Glu Val Ala Val Arg Met Leu Ser Arg Asn
305             310             315             320

Pro Lys Gly Phe Tyr Leu Phe Val Glu Gly Gly Arg Ile Asp His Gly
            325             330             335

His His Glu Thr Val Ala Tyr Arg Ala Leu Thr Glu Ala Val Met Phe
        340             345             350

Asp Ser Ala Val Asp Lys Ala Asp Lys Leu Thr Ser Glu Gln Asp Thr
        355             360             365

Met Ile Leu Val Thr Ala Asp His Ser His Val Phe Ser Phe Gly Gly
    370             375             380

Tyr Thr Gln Arg Gly Ala Ser Ile Phe Gly Leu Ala Pro Phe Lys Ala
385             390             395             400

Glu Asp Gly Lys Ser Phe Thr Ser Ile Leu Tyr Gly Asn Gly Pro Gly
            405             410             415

Tyr Lys Leu His Asn Gly Ala Arg Ala Asp Val Thr Glu Glu Glu Ser
```

```
                420             425             430
Ser Asn Pro Thr Tyr Gln Gln Gln Ala Ala Val Pro Leu Ser Ser Glu
        435                 440                 445
Thr His Ser Gly Glu Asp Val Ala Ile Phe Ala Arg Gly Pro Gln Ala
    450                 455                 460
His Leu Val His Gly Val Gln Glu Gln Asn Tyr Ile Ala His Val Met
465                 470                 475                 480
Ala Phe Ala Ala Cys Leu Glu Pro Tyr Thr Asp Cys Gly Leu Ala Ser
                485                 490                 495
Pro Ala Gly Gln Ser Ser Ala Val Ser Pro Gly
            500                 505

<210> SEQ ID NO 3
<211> LENGTH: 19
<212> TYPE: PRT
<213> ORGANISM: Artificial
<220> FEATURE:
<223> OTHER INFORMATION: Murine EAP Signal Sequence
<220> FEATURE:
<221> NAME/KEY: PEPTIDE
<222> LOCATION: (1)..(19)
<223> OTHER INFORMATION: Murine EAP Signal Sequence
<220> FEATURE:
<221> NAME/KEY: PEPTIDE
<222> LOCATION: (1)..(19)
<223> OTHER INFORMATION:

<400> SEQUENCE: 3

Met Trp Gly Ala Cys Leu Leu Leu Gly Leu Ser Leu Gln Val Cys
1               5                   10                  15

Pro Ser Val

<210> SEQ ID NO 4
<211> LENGTH: 41
<212> TYPE: DNA
<213> ORGANISM: Artificial
<220> FEATURE:
<223> OTHER INFORMATION: Synthetic oligo

<400> SEQUENCE: 4
gtataagctt gccaccatgt ggggagcctg cttgctgctg c                 41

<210> SEQ ID NO 5
<211> LENGTH: 38
<212> TYPE: DNA
<213> ORGANISM: Artificial
<220> FEATURE:
<223> OTHER INFORMATION: Synthetic Oligo

<400> SEQUENCE: 5
gttttctaga tcagcccggg ctcactgcac tgctctgg                     38

<210> SEQ ID NO 6
<211> LENGTH: 35
<212> TYPE: DNA
<213> ORGANISM: Artificial
<220> FEATURE:
<223> OTHER INFORMATION: Synthetic Oligo

<400> SEQUENCE: 6
actctctaga tcagggttca gccgccgcca tcagc                        35

<210> SEQ ID NO 7
<211> LENGTH: 35
```

```
<210> SEQ ID NO 7
<211> LENGTH: 35
<212> TYPE: DNA
<213> ORGANISM: Artificial
<220> FEATURE:
<223> OTHER INFORMATION: Synthetic Oligo C9415

<400> SEQUENCE: 7
cgcgaagctt gccaccatgt ggggagcctg cttgc                              35

<210> SEQ ID NO 8
<211> LENGTH: 36
<212> TYPE: DNA
<213> ORGANISM: Artificial
<220> FEATURE:
<223> OTHER INFORMATION: Synthetic Oligo C9416

<400> SEQUENCE: 8
ctcttctaga ctatcagccc gggctcactg cactgc                             36

<210> SEQ ID NO 9
<211> LENGTH: 24
<212> TYPE: PRT
<213> ORGANISM: Artificial
<220> FEATURE:
<223> OTHER INFORMATION: Human Preproinsulin signal peptide (GenBank
      GI:69300)
<220> FEATURE:
<221> NAME/KEY: PROTEIN
<222> LOCATION: (1)..(24)
<223> OTHER INFORMATION:

<400> SEQUENCE: 9

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 10
<211> LENGTH: 24
<212> TYPE: PRT
<213> ORGANISM: Artificial
<220> FEATURE:
<223> OTHER INFORMATION: Mouse Preproinsulin (SwissProt P01325)
<220> FEATURE:
<221> NAME/KEY: PEPTIDE
<222> LOCATION: (1)..(24)
<223> OTHER INFORMATION:

<400> SEQUENCE: 10

Met Ala Leu Leu Val His Phe Leu Pro Leu Leu Ala Leu Leu Ala Leu
1               5                   10                  15

Trp Glu Pro Lys Pro Thr Gln Ala
            20

<210> SEQ ID NO 11
<211> LENGTH: 20
<212> TYPE: PRT
<213> ORGANISM: Artificial
<220> FEATURE:
<223> OTHER INFORMATION: Immunoglobulin gamma 2a-chain V-region signal
      peptide (GenBank GI:12750776)
<220> FEATURE:
<221> NAME/KEY: PEPTIDE
<222> LOCATION: (1)..(20)
<223> OTHER INFORMATION:

<400> SEQUENCE: 11

Met Glu Arg His Trp Ile Phe Leu Phe Leu Phe Ser Val Thr Ala Gly
1               5                   10                  15
```

```
Val His Ser Gln
            20

<210> SEQ ID NO 12
<211> LENGTH: 20
<212> TYPE: PRT
<213> ORGANISM: Artificial
<220> FEATURE:
<223> OTHER INFORMATION: Rat interleukin 2 precursor signal peptide
      (SwissProt P17108)
<220> FEATURE:
<221> NAME/KEY: PEPTIDE
<222> LOCATION: (1)..(20)
<223> OTHER INFORMATION: Rat interleukin 2 precursor signal peptide
      (swissprot P17108)
<220> FEATURE:
<221> NAME/KEY: PEPTIDE
<222> LOCATION: (1)..(20)
<223> OTHER INFORMATION:

<400> SEQUENCE: 12

Met Tyr Ser Met Gln Leu Ala Ser Cys Val Ala Leu Thr Leu Val Leu
1               5                   10                  15

Leu Val Asn Ser
            20

<210> SEQ ID NO 13
<211> LENGTH: 529
<212> TYPE: PRT
<213> ORGANISM: Artificial
<220> FEATURE:
<223> OTHER INFORMATION: Full length mouse EAP polypeptide (GenBank
      GI:192977)

<400> SEQUENCE: 13

Met Trp Gly Ala Cys Leu Leu Leu Gly Leu Ser Leu Gln Val Cys
1               5                   10                  15

Pro Ser Val Ile Pro Val Glu Glu Asn Pro Ala Phe Trp Asn Arg
            20                  25                  30

Lys Ala Ala Glu Ala Leu Asp Ala Ala Lys Lys Leu Lys Pro Ile Gln
        35                  40                  45

Thr Ser Ala Lys Asn Leu Val Ile Leu Met Gly Asp Gly Met Gly Val
    50                  55                  60

Ser Thr Val Thr Ala Thr Arg Ile Leu Lys Gly Gln Gln Gln Gly Leu
65                  70                  75                  80

Ser Gly Pro Glu Thr Gln Leu Ala Met Asp Arg Phe Pro His Met Ala
                85                  90                  95

Leu Ser Lys Thr Tyr Asn Thr Asp Lys Gln Ile Pro Asp Ser Ala Gly
            100                 105                 110

Thr Gly Thr Ala Phe Leu Cys Gly Val Lys Thr Asn Met Lys Val Ile
        115                 120                 125

Gly Leu Ser Ala Ala Ala Arg Phe Asn Gln Cys Asn Thr Thr Trp Gly
    130                 135                 140

Asn Glu Val Val Ser Val Met His Arg Ala Lys Lys Ala Gly Lys Ser
145                 150                 155                 160

Val Gly Val Val Thr Thr Thr Ser Val Gln His Ala Ser Pro Ala Gly
                165                 170                 175

Thr Tyr Ala His Thr Val Asn Arg Gly Trp Tyr Ser Asp Ala Gln Met
            180                 185                 190

Pro Ala Ser Ala Leu Gln Asp Gly Cys Lys Asp Ile Ser Thr Gln Leu
        195                 200                 205
```

```
Ile Ser Asn Met Asp Ile Asp Val Ile Leu Gly Gly Arg Lys Phe
    210             215                 220
Met Phe Pro Lys Gly Thr Pro Asp Gln Glu Tyr Pro Thr Asp Thr Lys
225             230                 235                 240
Gln Ala Gly Thr Arg Leu Asp Gly Arg Asn Leu Val Gln Glu Trp Leu
                245                 250                 255
Ala Lys His Gln Gly Ala Arg Tyr Val Trp Asn Arg Ser Glu Leu Ile
            260                 265                 270
Gln Ala Ser Leu Asn Arg Ser Val Thr His Leu Met Gly Leu Phe Glu
        275                 280                 285
Pro Asn Asp Met Lys Tyr Glu Ile His Arg Asp Pro Ala Gln Asp Pro
    290                 295                 300
Ser Leu Ala Glu Met Thr Glu Val Ala Val Arg Met Leu Ser Arg Asn
305                 310                 315                 320
Pro Lys Gly Phe Tyr Leu Phe Val Glu Gly Gly Arg Ile Asp His Gly
                325                 330                 335
His His Glu Thr Val Ala Tyr Arg Ala Leu Thr Glu Ala Val Met Phe
            340                 345                 350
Asp Ser Ala Val Asp Lys Ala Asp Ile Arg Thr Ser Glu Gln Asp Thr
        355                 360                 365
Met Ile Leu Val Thr Ala Asp His Ser His Val Phe Ser Phe Gly Gly
370                 375                 380
Tyr Thr Gln Arg Gly Ala Ser Ile Phe Gly Leu Ala Pro Phe Lys Ala
385                 390                 395                 400
Glu Asp Gly Lys Ser Phe Thr Ser Ile Leu Tyr Gly Asn Gly Pro Gly
                405                 410                 415
Tyr Lys Leu His Asn Gly Ala Arg Ala Asp Val Thr Glu Glu Ser
            420                 425                 430
Ser Asn Pro Thr Tyr Gln Gln Gln Ala Cys Val Pro Leu Ser Ser Glu
        435                 440                 445
Thr His Ser Gly Glu Asp Val Ala Ile Phe Ala Arg Gly Pro Gln Ala
    450                 455                 460
His Leu Val His Gly Val Gln Glu Gln Asn Tyr Ile Ala His Val Met
465                 470                 475                 480
Ala Phe Ala Ala Cys Leu Glu Pro Tyr Thr Asp Cys Gly Leu Ala Ser
                485                 490                 495
Pro Ala Gly Gln Ser Ser Ala Val Ser Pro Gly Tyr Met Ser Thr Leu
            500                 505                 510
Leu Cys Leu Leu Ala Gly Lys Met Leu Met Leu Met Ala Ala Ala Glu
        515                 520                 525
Pro
```

US 7,169,913 B2

ENGINEERED SECRETED ALKALINE PHOSPHATASE (SEAP) REPORTER GENES AND POLYPEPTIDES

FIELD OF THE INVENTION AND INTRODUCTION

This application claims priority to U.S. Provisional application No. 60/293,186, filed May 25, 2001, the entire contents of which are hereby incorporated by reference.

The invention relates to nucleic acids that encode reporter genes capable of being used in long term expression studies and vectors comprising them. Methods for producing vectors for long term expression and the expression systems that incorporate these reporter genes and other transgenes are also included in the invention, as well as the recombinant polypeptides encoded by the reporter genes.

Many gene transfer vectors and systems are intended to express genes for extended periods of time, i.e. over weeks or months. This is especially the case where the transgene encodes a functional protein or therapeutic protein. Methods to evaluate the persistence of expression using these gene transfer vectors usually employ detectable reporter genes. However, the protein products of currently used reporter genes lack one or more of several characteristics, making them inappropriate for studying long term expression in an animal. This invention provides new and useful reporter genes, nucleic acids, expression vectors, polypeptides, and methods of expressing transgenes that are particularly suited for long term expression. Compared to the prior reporter genes, which may express detectable protein up to 20 days or so, the reporter genes of the invention express detectable protein levels for more than about a month, or to at least about 9 months. The expression levels are also stable over this period. Furthermore, the proteins from reporter genes of the invention can be detected in a number of cell types and tissues, where detection using other reporter genes has proven to be difficult.

DISCUSSION OF RELATED TECHNOLOGY

Reporter genes have been used to analyze the expression of transgenes from various vectors. Reporter genes that have been used in animal models encode exogenous cytoplasmic or secreted proteins, such as bacterial β-galactosidase, insect luciferase, human growth hormone, human erythropoietin, and human secreted alkaline phosphatase (SEAP). These reporter genes often are used for transient expression studies or tissue-specific expression studies. However, the proteins they encode are typically immunogenic. They can also elicit a cytotoxic T-lymphocyte response or a neutralizing antibody response that suppresses detection, leading to inaccurate reporter gene expression data (see Tripathy et al., Nature Medicine 2:545–50 (1996); and Yang et al., Gene Therapy 3:137–44 (1996)).

From these deficiencies alone, one can conclude that the reporter genes currently used were not really designed for and have not been shown to be amenable to longer term expression studies. When longer term expression data is needed, a reporter gene that continues to express, can be detected, avoids the animal's immune response mechanisms, and does not alter cell physiology is important. To date, such a reporter gene has not been adequately provided. In fact, experimental systems have been modified to accommodate the existing reporter genes by, for example, using immuno-deficient animals.

One reporter gene, the SEAP gene noted above, is derived from the native human placental alkaline phosphatase (hPLAP). The amino acid sequence typically used for its reporter gene function differs from the native gene by a deletion of C-terminal residues, which converts the membrane-bound protein into a secreted protein (Berger, et al., Gene 66, 1–10 (1988)). While the SEAP reporter gene has been used in a number of expression systems, the selection of alkaline phosphatase-derived reporter genes often results in detection problems, especially when long term expression levels are analyzed. For example, background alkaline phosphatase activity can be present in mammalian tissue. Also, inhibitors of alkaline phosphatase action can be present in certain mammalian tissues. These and other shortcomings of the SEAP gene and other alkaline phosphatase-derived reporter genes have yet to be overcome.

SUMMARY OF THE INVENTION

The invention encompasses alkaline phosphatase (AP) reporter genes and nucleic acid sequences encoding a mammalian alkaline phosphatase activity. The alkaline phosphatase activity is capable of being detected for at least about one month after being inserted into a cell as a transgene. Preferably, expressing the alkaline phosphatase-encoding sequences of the invention in a cell results in alkaline phosphatase activity that can be detected for more than about 40 days, or more than about 60 days, or more than about 90 days, or more than about 120 days, or more than about 180 days, or more than about 270 days. Typically, but not necessarily, the alkaline phosphatase activity is detected by measuring the protein levels or AP activity of a serum or tissue sample from a mammal containing the cell with the transgene, or measuring the media from a cultured cell containing the transgene. Other methods of detection can be used, including immunochemical assays.

In a preferred embodiment, the mammalian alkaline phosphatase activity consists of, consists essentially of, or comprises a polypeptide amino acid sequence of SEQ ID NO: 1 or SEQ ID NO: 2. A polypeptide or protein consisting essentially of the amino acid sequence of SEQ ID NO: 1 or SEQ ID NO: 2 will contain the amino acid sequence of SEQ ID NO: 1 or SEQ ID NO: 2 and one or more amino acid differences in the sequence that do not change the basic and novel characteristics of the protein. As described, some of the basic and novel characteristics of the mSEAP polypeptide of SEQ ID NO: 2 or the AP activity of SEQ ID NO: 1 are the ability to be expressed and detected in long term expression studies (here long term can mean one of over 30 days, 40 days, 60 days, 90 days, 180 days, or 270 days), the ability to be detected long term in immuno-competent mammals, and/or the ability to be expressed long term at stable levels (levels that do not change more than about 5-fold or more than about 10-fold). None of the prior alkaline phosphatase, embryonic alkaline phosphatase, or secreted embryonic alkaline phosphatase proteins or polypeptides possess even one of these novel characteristics. Any isolated or purified cDNA or nucleic acid that encodes a polypeptide of SEQ ID NO: 1 or SEQ ID NO: 2 is included in the invention. Also, the polypeptide of SEQ ID NO: 1 can be joined with an appropriate mammalian or murine signal sequence so the AP activity is secreted from the cell. Any of a variety of signal sequences can be used, including that of SEQ ID NO: 3, 9, 10, 11, or 12. Fusion proteins where the amino acid sequence of SEQ ID NO: 1 or 2 is used are also included in the invention provided they do not include a fusion generating or encoding the exact amino acid sequence of SEQ ID NO: 13. Furthermore, derivatives and mutants of SEQ ID NO: 1 or 2 are included in the invention and specific, non-limiting examples of the mutants are presented. One series of mutants includes polypeptides where about 1 to about 5 amino acids are deleted from the C-terminal end of SEQ ID NO: 1 or 2. One skilled in the art can use numerous methods to create other derivatives or mutations in SEQ ID NO: 1 or 2 and the degenerate variants encoding SEQ ID NO: 1 or 2 as well as the derivative polypeptides and mutant polypeptides themselves. The derivative polypeptides, and the nucleic acids encoding them, also possess or encode polypeptides that possess one or more of the novel long term expression characteristics listed above, but do not include a polypeptide or SEQ ID NO: 13.

In another aspect, the invention comprises methods for analyzing expression systems and vectors for use in gene transfer experiments and protocols. For example, a gene transfer vector that comprises a reporter gene or nucleic acid sequence of the invention can be introduced into an animal. By detecting reporter gene expression levels, the vector system components and methods used to introduce and prepare the vector for administration can be tested and/or optimized for long term use in expressing a transgene. The methods can be used to select a type of expression vector, specific regulatory or combinations of sequences used in expression vectors, and protocols for administering transgenes to animals. For example, the properties or desirability of selected gene expression regulatory elements (DNA or RNA sequences in cis, or protein, DNA, or RNA factors in trans) can be analyzed and/or optimized by using the nucleic acids and methods of the invention. Both the selection and analysis processes and the vectors and compositions selected or that result from the processes are specifically included in this invention. In a preferred embodiment of this aspect, a vector is prepared and introduced into an animal or cell. The vector comprises a reporter gene or nucleic acid of the invention linked to an appropriate promoter or promoter/enhancer so that the reporter gene is expressed. The alkaline phosphatase expression levels are analyzed for at least about one month and optionally compared to controls, such as different vectors comprising the reporter gene. The results of the expression levels for the period of at least about one month are then used to select or confirm that a vector is appropriate or desirable for the administration of a particular transgene. The same methods can be used for periods of at least about 40 days, about 60 days, about 90 days, about 120 days, about 180 days, or about 270 days. The selected vector with particular transgene can then be used for other purposes where long term expression is desired, such as treatment for disease or physiological condition or production of a certain phenotype in an animal. Similarly, administration methods can be analyzed and compared, as for example intramuscular injection, intratumoral injection, intradermal injection, inhalation, or other routes of administration. The type of vector used can also be analyzed, such as naked plasmid, adenoviral vector, adeno-associated virus vector, retroviral vector, and lentiviral vector. The invention is also directed to a reporter vector containing the mSEAP sequence according to the present invention. Such reporter vector may be derived from a prokaryotic plasmid, such as pBR322 or the pUC plasmid. A reporter plasmid can also contain a resistance gene or other marker, such as, inter alia, ampicillin, tetracycline, or kanamycin resistance genes. A reporter plasmid can also contain an origin of replication that is functional in eukaryotic cells, such as the SV40 ori. Preferably, a reporter vector of the invention contains a multiple cloning site upstream of the mSEAP encoding sequence. The reporter vector may be used as a negative control or be used to clone a promoter for characterization, and thus may lack a eukaryotic promoter and enhancer sequence. Alternatively, a reporter vector comprises the mSEAP sequence according to the present invention operably linked to a promoter and a enhancer sequence, and are used as positive controls or as a reference for comparing the activity of one or more promoters and/or one or more enhancers. Any combination of vector, administration method, and/or compositions used for administration can also be selected or optimized in employing methods to use the reporter vector. In a preferred embodiment, the invention includes a method of expressing a transgene comprising selecting a vector for expressing the transgene, inserting a nucleic acid comprising, consisting essentially of, or consisting of a mSEAP sequence, such as those of SEQ ID NO: 1 or 2, into the vector, whereby the vector causes the expression of or is capable of expressing a mSEAP polypeptide, administering the vector containing the mSEAP sequence to a cell or mammal, detecting the expression of mSEAP polypeptide for a period of about 40 days or more after administering the vector, employing the selected vector without substantial changes in its nucleotide sequence to deliver a transgene product to a cell or animal. The vector without substantial changes in its nucleotide sequence will be the same vector with optional sequence modifications due to the insertion of a different transgene sequence or use of different insertion sites, or sequence modifications that do not result in a substantial change in the expression of the transgene, or sequence modifications that do not substantially effect the function of the vector. As described for this aspect and any aspect of the invention, the transgene can be any number of sequences that encode a polypeptide or protein or any number of sequences that encode a functional transcript. Functional transcripts include, for example, anti-sense nucleic acids, ribozymes, and other nucleic acids intended to act within a cell. The protein or polypeptide-encoding sequences can be those that encode a therapeutic activity or an activity that performs a function in the cell. Numerous transgenes encompassing these activities have been used and can be selected for use with the invention, and the selection of the transgene itself does not limit the scope or practice of the invention.

The vectors that can be used include any organism, cell or composition that allows a nucleic acid to be introduced into a cell. For example, the vectors can be nucleic acids, plasmids, cosmids, recombinant viral vectors, liposomes bearing nucleic acids or recombinant viruses, recombinant or genetically modified cells, and compositions comprising these examples or any combination of these examples. Furthermore, the nucleic acids and vectors can be used with any cell type, cell line, primary cell culture, tumor cell, or other cell from or derived from an animal. A particular embodiment of a cell comprising an mSEAP-encoding nucleic acid, mSEAP-containing vector, or an mSEAP polypeptide of the invention, is a model cell for studying a disease or the treatment of disease. For example, a model tumor cell expressing an mSEAP of the invention can be inserted into an animal. The model tumor cell can be a human cell, a mouse cell, a rat cell, or any appropriate mammalian or animal cell. A change in mSEAP expression level can be assayed during a variety of treatment regimens or compounds given to the animal. Reduced expression levels, or changes in expression levels, can then detect a treatment or compound that influences tumor growth, volume, or cell metabolism (see, for example, Nilsson, et al. Cancer Chemotherapy and Pharmacology 49:93–100 (2001)). Thus, a cell of the invention can be a tumor cell or any other cell inserted into an animal as well as a cultured cell. Both in vivo and in vitro methods to screen or identify a compound for an effect on cell viability, cell protein expression, cell division, apoptosis, or other property can incorporate or use an mSEAP polypeptide or vector comprising an mSEAP reporter gene of the invention.

The present invention is also directed to a method of monitoring tumor growth and/or detecting a response to an anti-cancer drug treatment, such as an anti-angiogenic therapeutic, using the mSEAP of the present invention as the in vivo reporter gene. In one embodiment, a mouse model in which the tumor cell line is stably transfected with a constitutively expressed mSEAP sequence according to the present invention is used. The present invention is further directed to a method of monitoring tumor growth comprising injecting athymic nude mice or any susceptible animals with cells from cancer tissue or cell lines, which are stably transfected with the mSEAP of the present invention, and measuring the level of mSEAP expressed to monitor the amount of of volume of tumor cells and/or tumor growth. In effect, the level of mSEAP is known to be proportional to the number of the tumor cells in the animal or in the culture medium used. Thus, a variety of in vivo and in vitro cell analysis and measurement assays and method can employ the mSEAP reporter gene and polypeptide of the invention. The present invention is further directed to a method of monitoring or screening the efficiency of one or more therapapeutic agents, such a chemotherapeutic or anti-angiogenic therapeutic, comprising injecting athymic nude mice or any susceptible animals with cells from cancer tissue or cell lines that are stably transfected with the mSEAP of the present invention, treating said mice or animals with the therapeutic agent or anticancer drug to be tested, and measuring the level of mSEAP expressed to monitor tumor growth and/or volume, and thus the efficiency of the therapeutic or anticancer drug treatment. The response to the treatment may be evaluated by measuring mSEAP levels in the blood during the course of the treatment. For example, the method according to the present invention can be advantageously used to screen for new anticancer therapeutics against intraperitoneal tumors, such as ovarian carcinomas, or subcutaneous tumors. Chemotherapeutic agents and combinations of agents that may be screened by using a method according to the present invention include the platinum containing compounds, such as cisplatin, carboplatin, and oxaliplatin, alone or in combination with cyclophosphamide or a taxol analogue paclitaxel, or taxotere. The correlation between the tumor growth and mSEAP levels may be evaluated by measuring the tumor volume after death and dissection of the tumor, or on a live animal, when the tumor is accessible (i.e., subcutaneous), and measuring the levels of mSEAP in the plasma. Therefore, the levels of mSEAP can provide an appropriate marker of tumor growth and/or the response to the anticancer drug treatment.

The invention also provides nucleic acids that encode AP activity and comprise one or more nucleotide substitution, deletion, or addition changes from a nucleotide sequence encoding a polypeptide having the amino acid sequence of SEQ ID NO: 1 or 2, as well as the AP proteins themselves. The AP activity of these proteins allows for the long term expression analysis noted above, for over about one month, or over about 40 days, or about 60 days, or about 90 days, or about 180 days, or about 270 days. Alternatively, the AP activity in cells or animals with introduced nucleic acid sequences is relatively stable over these periods of time, i.e. the levels do not change more than about 5 fold, or more than about 10 fold from the levels detectable after day 10. These nucleic acids and proteins can be produced by any of numerous mutation generating techniques known in the art. The proteins and nucleic acids can be tested for their ability to possess or encode the long term expression activity by the same methods or types of methods described throughout this disclosure.

BRIEF DESCRIPTION OF THE DRAWINGS

FIGS. 1A and 1B depicts a sequence alignment between hSEAP (SEQ ID NO: 14; translated from GI 2190731 of GenBank), the murine full-length alkaline phosphatase (AP) protein, mEAP (SEQ ID NO: 13; translated from GE 192976 of GenBank), and an engineered mammalian AP of the invention, mSEAP (SEQ ID NO: 2; as translated from the nucleotide sequencing data verified by inventor). The "Consensus" sequence listed at the bottom line is the same sequence as the mSEAP (SEQ ID NO: 2).

FIG. 7 shows the amino acid sequence of mSEAP, with underlined amino acids that can be replaced by conservative amino acid substitutions to create exemplary mutants or derivative polypeptides of a mSEAP sequence of the invention or of the sequences of SEQ ID NO: 1 or 2.

DETAILED DESCRIPTION OF EXEMPLARY EMBODIMENTS

Figure 1A:
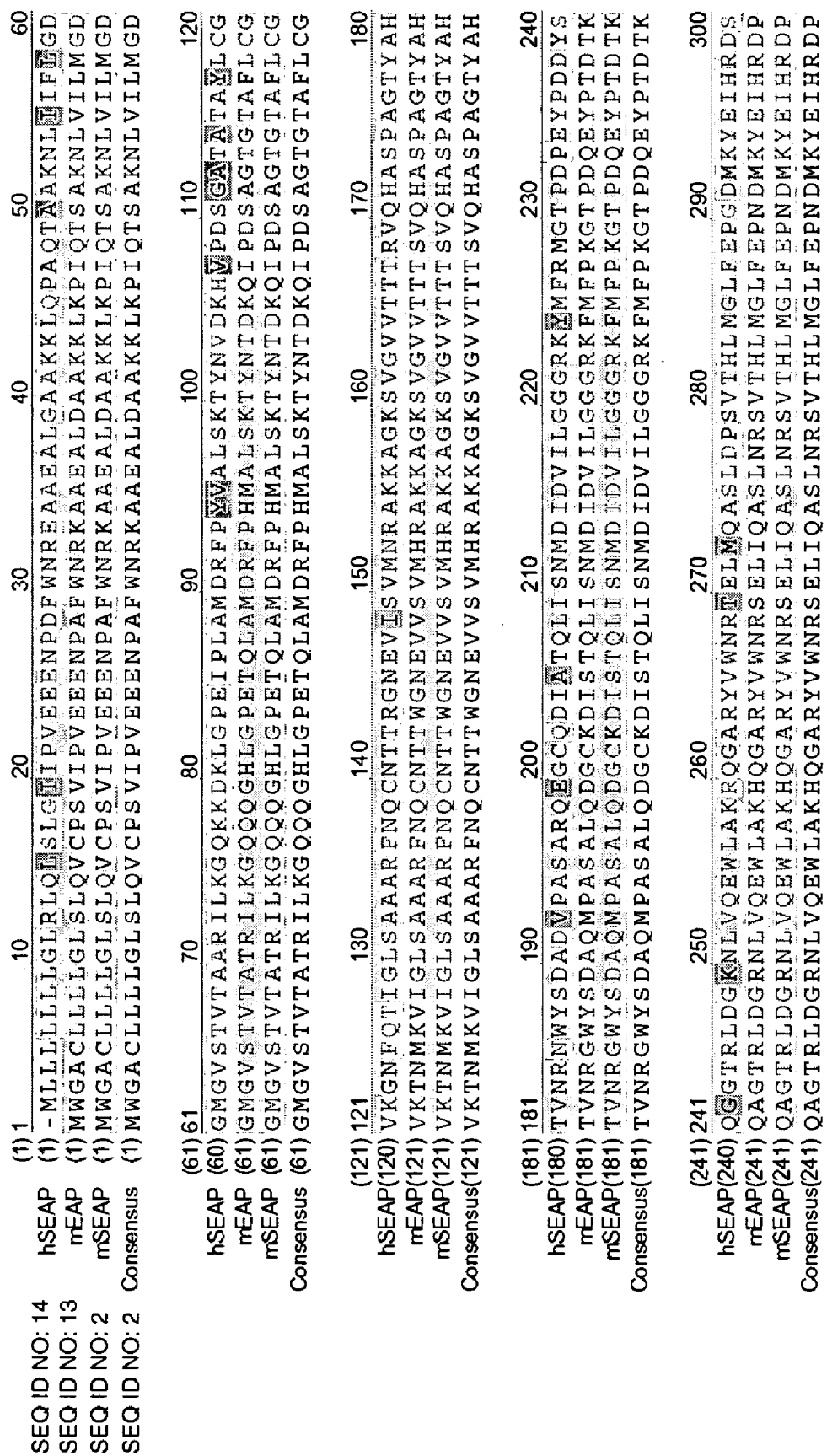

Each of the references (publication, article, web page, information source, GenBank or SwissProt sequence, or patent document, for example) referred to in this specification is hereby specifically incorporated herein by reference, in its entirety. Furthermore, each reference or any combination of references can be relied on and used, in whole or in part, to make, use, and test embodiments of the invention or specific examples described here. As this statement applies to each and every reference, document, or source of information, this specification will not repeat the incorporation by reference. This statement operates to effectively incorporate by reference in their entirety each and every reference (as defined above) listed or referred to in the specification.

In making and using aspects and embodiments of this invention, one skilled in the art may employ conventional molecular biology, virology, microbiology, and recombinant DNA techniques. Exemplary techniques are explained fully in the literature and are well known in the art. For example, one may rely on the following general texts to make and use the invention: Sambrook et al., *Molecular Cloning: A Laboratory Manual*, Second Edition (1989) Cold Spring Harbor Laboratory Press, Cold Spring Harbor, N.Y. and Sambrook et al. Third Edition (2001); *DNA Cloning: A Practical Approach*, Volumes I and II (D. N. Glover ed. 1985); *Oligonucleotide Synthesis* (M. J. Gaited. 1984); *Nucleic Acid Hybridization* (B. D. Hames & S. J. Higgins eds. (1985)); *Transcription And Translation* Hames & Higgins, eds. (1984); *Animal Cell Culture* (RI. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (2001), Coligan et al. (eds.), *Current Protocols in Immunology*, John Wiley & Sons, Inc. (2001); Dracopdi et al., *Current Protocols in Human Genetics*, John Wiley & Sons, Inc. (2001), W. Paul et al. (eds.) *Fundamental Immunology*, Raven Press; E. J. Murray et al. (ed.) *Methods in Molecular Biology: Gene Transfer and Expression Protocols*, The Humana Press Inc. (1991); and J. E. Celis et al., *Cell Biology: A Laboratory Handbook*, Academic Press (1994).

As used herein, a "vector" means any nucleic acid or nucleic acid-bearing particle or composition, cell, or organism capable of being used to transfer a nucleic acid into a host cell. The term "vector" includes both viral and nonviral products and means for introducing the nucleic acid into a cell. A "vector" can be used in vitro, ex vivo, or in vivo. Non-viral vectors include plasmids, cosmids, and can comprise liposomes, electrically charged lipids (cytofectins), DNA-protein complexes, and biopolymers, for example. Viral vectors include retroviruses, lentiviruses, adeno-associated virus, pox viruses, baculovirus, reoviruses, vaccinia viruses, herpes simplex viruses, Epstein-Barr viruses, and adenovirus vectors, for example.

A "nucleic acid" is a polymeric compound comprised of covalently linked nucleotides, from whatever source. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The term "nucleic acid" also captures sequences that include any nucleotide base analogue or synthetic nucleotide base.

Percent "identity" between two nucleic acids or two polypeptide molecules refers to the percent defined by a comparison using a basic blast (blastn, blastp, blastx, tblastn, or tblastx, for example) search at the default setting (see, for example, NOBI BLAST home page ncbi.nlm.nih.gov/BLAST/). "Homology" can be determined by a direct comparison of the sequence information between two polypeptide molecules by aligning the sequence information and using readily available computer programs. Alternatively, homology can be determined by hybridization of polynucleotides under conditions allowing for the formation of stable duplexes between homologous regions and detecting the identifying double-stranded nucleic acid.

One or more amino acid residues within a sequence can be substituted by another amino acid of a similar polarity, which acts as a functional equivalent when the substitution results in no significant change in activity in at least one selected biological activity or function. A derivative polypeptide will be a functional equivalent of a given amino acid sequence. For example, one or more substitutions at the positions indicated (by underlining) in FIG. 7 can be made in SEQ ID NO: 1 or 2 to produce a functionally equivalent, derivative polypeptide. Truncations from the C-terminal end of SEQ ID NO: 1 or 2 can also be made to produce a functionally equivalent, derivative polypeptide. Conservative substitutions for an amino acid within a sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar, neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Alterations of an amino acid with another amino acid from the same class will not substantially effect activity, apparent molecular weight as determined by polyacrylamide gel electrophoresis, or significantly affect the isoelectric point.

"Isolated," when referring to a nucleic acid, gene, or vector, means that the indicated molecule or product is present in the substantial absence of other biological macromolecules of the same type, or that the indicated molecule or product is present after being subjected to at least one purification step or procedure, such as cell lysis, precipitation, size separation, extraction, chromatography, or any other technique known in the art. Thus, an "isolated nucleic acid molecule that encodes a particular polypeptide" can be to a nucleic acid molecule substantially free of other nucleic acid molecules that do not encode the particular polypeptide. However, the preparation or sample containing the molecule may include other components of different types. In addition, "isolated" can also mean that a particular molecule or product has been purified by at least one purification step or procedure from its ultimate or original source.

As used herein, a "reporter gene" can refer to a nucleic acid that encodes a detectable polypeptide or protein, such as AP, or can refer to the protein product of that expressed nucleic acid. Thus, the mSEAP reporter gene and protein can mean the genomic DNA encoding EAP modified to become or encode a mSEAP polypeptide, or a modified cDNA encoding a mSEAP, or the mSEAP protein itself (the mSEAP reporter gene product). The novel mSEAP reporter gene and protein of the invention specifically include SEQ ID NO: 1, SEQ ID NO: 1 in combination with a mammalian signal sequence at the N-terminal end, SEQ ID NO: 1 in combination with a murine signal sequence at the N-terminal end, SEQ ID NO: 2, any of the above with about 1 to about 5 amino acids deleted from the C-terminal end, and any derivative or mutant of SEQ ID NO: 1 or 2 that has not previously been disclosed to the public or in an application for patent, as well as the nucleic acids that encode these sequences. As used herein, a derivative or mutant can be a sequence with about 80% identity, about 90% identity, or about 95% identity with SEQ ID NO: 1 or 2 using a blast comparison at the default settings, as well as nucleotide sequences encoding them. A derivative polypeptide can also possess the long term expression characteristics of being detectable over at least about 40 days, or at least about 60 days, or at least about 180 days, or at least about 270 days after insertion into a cell. The mSEAP polypeptides or reporter gene products of the invention do not include a polypeptide with the exact amino acid sequence of SEQ ID NO: 13.

Numerous gene transfer methods and techniques can be used in conjunction with the invention beyond those specifically described. Many of the references listed can be used in selecting an appropriate gene transfer technique, composition, or delivery method. Reporter genes have been used in a number of mammalian test subjects, including mouse, rabbit, cat, dog, primates, and humans. One of skill in the art is familiar with the techniques and methods appropriate for these mammalian test subjects. See, for example, Rosenberg et al., *New Eng. J. Med.* 323: 570–78 (1990); Cavazzana-Calvo et al., *Science* 288: 669–72 (2000); Dobson et al., *Brit. Med. J.* 320: 1225 (2000); Buckley et al., *Nature Med.* 6: 623–24 (2000); and the general texts and references listed above.

Some Experimentally Determined Properties and Characteristics of mSEAP

We have engineered the mouse embryonic alkaline phosphatase (mEAP) gene to be amenable for long term expression studies and the analysis of gene transfer methods and vectors. In so doing, we have addressed or solved several problems relating to the use of reporter genes in long term expression analysis. For example, the background AP activity in some animal tissue is quite high, for example plasma from mice. Heating plasma samples at 65° C. for 5 to 30 minutes can reduce the background from tissue non-specific alkaline phosphatase (TNAP) activity. Furthermore, inhibitors, such as L-homoarginine, can be used to reduce background TNAP activity. Pretreatment with heat and/or inhibitors is commonly used with AP activity assays. (Cullen and Malim, Meth. Enzymol. 216:362–368 (1992)). Until now, it was not known whether an engineered form of mEAP would be thermostable enough and resistant-enough to TNAP inhibitors for use as a reporter gene. Furthermore, it was not known if a reporter gene, and particularly an AP reporter gene, could be expressed and detected over long periods of time. Since the mEAP protein is naturally expressed in embryonic cells in mice, the expression of the engineered mSEAP protein may be subject to an endogenous or physiological regulation that shuts it off, rendering it useless as a reporter gene.

The mSEAP reporter gene sequences, nucleic acids, and proteins of the invention are the first that can be expressed and detected over several months in the classical laboratory, immuno-competent mammal after somatic gene transfer. The same vectors and nucleic acids can be used in a number of mammals, including, but not limited to, mouse, rat, pig, rabbit, goat, cow, sheep, macaque, cynomolgus macaque, and human. The freedom to use immuno-competent animals or to avoid treatments that inhibit the immune response reduces the complexity of the protocol, reduces the added risk to the animal, and reduces the cost of gene transfer experiments. Thus, the invention provides at least an economic advantage compared to other available methods for analyzing long term expression. The invention also provides the advantage of analyzing expression in a physiologically normal patient or animal. In addition, AP activity or the presence of the mSEAP protein can be assayed by several simple techniques, including those employing chemiluminescent, fluorescent, or other detectable substrates and assays.

Figure 3:
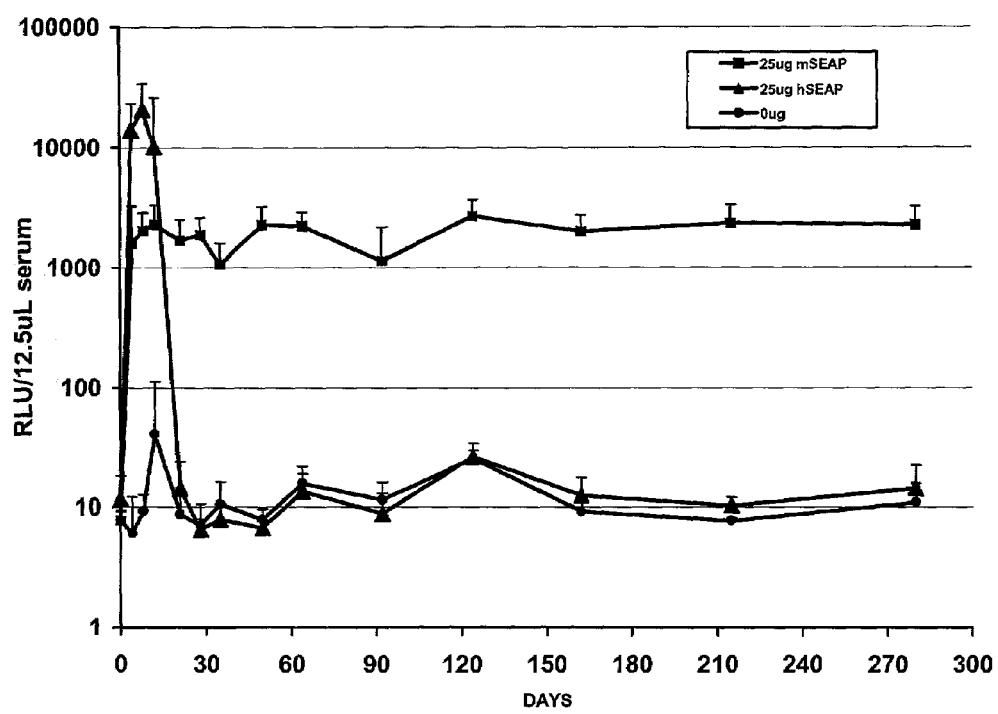
FIG. 3 shows the expression levels of alkaline phosphatase activity (AP) following introduction of transgene in Balb/C mice. AP activity is measured by sampling 12.5 µl of serum with the phosphalight kit (Tropix; Bedford, Mass.). The boxes represent the expression following introduction of 25 µg of plasmid DNA comprising an engineered mSEAP reporter gene of the invention. The triangles represent the expression levels following the introduction of 25 µg of the hSEAP reporter gene known in the art. The circles represent control where no plasmid DNA was used in the same injection vehicle. The vector is introduced to the mice by intramuscular injection enhanced by electric pulses.
Figure 4:
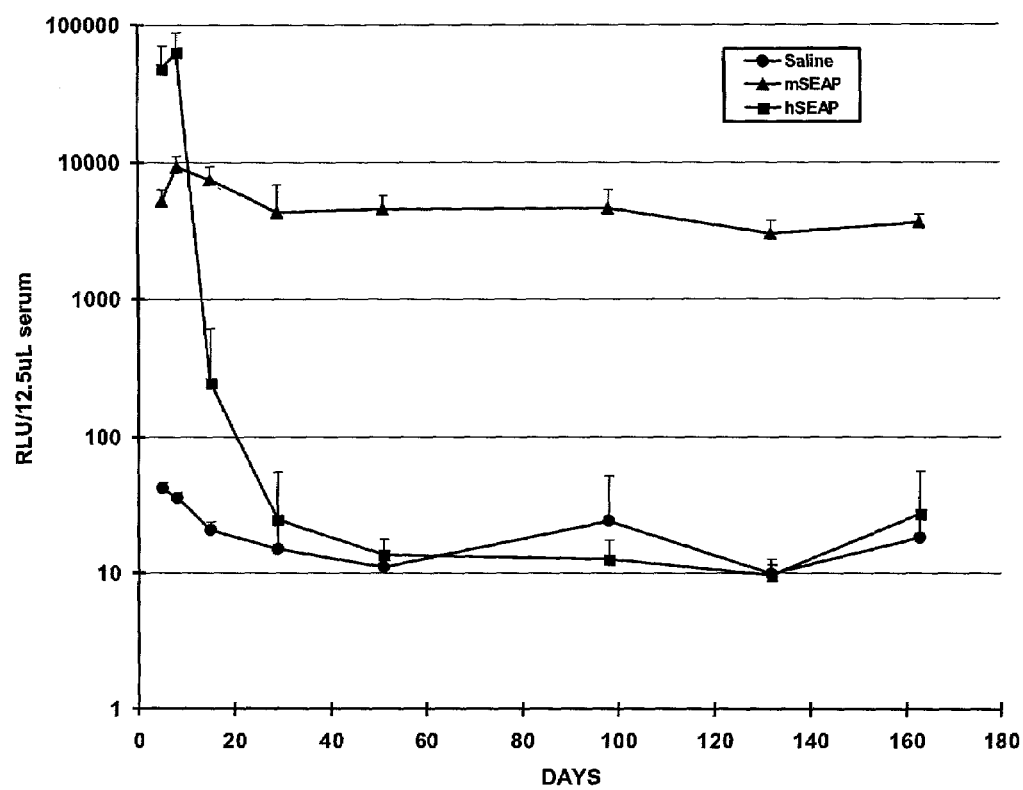
FIG. 4 shows the expression levels of alkaline phosphatase activity following introduction of transgene in C57/BL6 mice. The experimental details are the same as in FIG. 3. The boxes represent the expression following introduction of 25 µg of plasmid DNA comprising the hSEAP reporter gene known in the art. The triangles represent the expression levels following the introduction of 25 µg of a mSEAP reporter of the invention. The circles represent control where no plasmid DNA was used in the same vehicle.

We have demonstrated the use and advantages of the invention in an intramuscular gene transfer experiment using immuno-competent mice. For example, FIG. 3 shows that the level of expression of mSEAP reporter genes of the invention are stable over more than 250 days. In contrast, other reporter genes show a level of expression that drops after 21 days and the levels vary exponentially within the period after the initial ability to detect the activity. The result is consistent in two strains of mice with differing genetic backgrounds (Balb/C and C57/BL6). The lower activity of mSEAP is due to the presence of alkaline phosphatase inhibitors present in the detection kit (PhosphaLight, Tropix; Bedford, Mass.), which affect mSEAP activity but not hSEAP activity (data not shown).

We have also demonstrated that an immune response against hSEAP is the probable cause of the drop in hSEAP activity because we detected anti-hSEAP antibodies in mice injected with plasmid encoding hSEAP (see Table 1).

TABLE 1

|  | 1<br>64 ng/ml<br>mAb<br>(Sigma) | 2<br>Neg<br>control:<br>serum | 3<br>CMV-<br>hSEAP<br>#1 | 4<br>CMV-<br>hSEAP<br>#2 | 5<br>CMV-<br>hSEAP<br>#3 | 6<br>CMV-<br>hSEAP<br>#4 | 7<br>CMV-<br>hSEAP<br>#5 | 8<br>positive<br>control:<br>mAb in<br>neg serum |
|---|---|---|---|---|---|---|---|---|
| undiluted | 0.486 | 0.036 | 0.473 | 0.52 | 0.488 | 0.4 | 0.518 | 0.546 |
| 1:2 | 0.487 | 0.036 | 0.539 | 0.525 | 0.532 | 0.358 | 0.576 | 0.439 |
| 1:4 | 0.424 | 0.041 | 0.551 | 0.497 | 0.53 | 0.344 | 0.512 | 0.341 |
| 1:8 | 0.282 | 0.033 | 0.469 | 0.434 | 0.484 | 0.264 | 0.395 | 0.209 |
| 1:16 | 0.169 | 0.022 | 0.328 | 0.369 | 0.4 | 0.199 | 0.371 | 0.123 |
| 1:32 | 0.091 | 0.018 | 0.275 | 0.3 | 0.309 | 0.118 | 0.262 | 0.071 |
| 1:64 | 0.047 | 0.01 | 0.167 | 0.217 | 0.215 | 0.077 | 0.167 | 0.042 |
| 0 | 0.007 | 0.005 | 0.006 | 0.006 | 0.005 | 0.007 | 0.007 | 0.009 |

In Table 1, the detection by ELISA of anti-hSEAP antibodies in mice serum after i.m. electrotransfer of 25 µg plasmid containing DNA encoding hSEAP driven by the cytomegalovirus immediate early gene promoter (CMV) is shown. Microplates are coated with purified hPLAP (SIGMA, St. Louis, Mo.) and incubated with serum of mice injected with saline (neg serum: row #2) or hSEAP encoding plasmid (CMV-hSEAP, rows #3–7), or with anti-hPLAP monoclonal antibody diluted in PBS (row #1) or serum of non injected mice (row #8). Anti-hSEAP antibodies are detected by an anti-mouse antibody-HRP conjugate. After reaction with TMB the absorbance is read at 450 nm. Comparing the results of the negative control serum, row #2, with those of row # 3–7 shows that for each of the samples where hSEAP plasmid is injected and then expressed (row # 3–7) there are detectable levels of anti-hSEAP antibodies. This indicates that using the hSEAP reporter gene deleteriously results in the production of antibodies, confounding the results of expression assays and inappropriately inducing an immune response in the animal tested.

Figure 5:
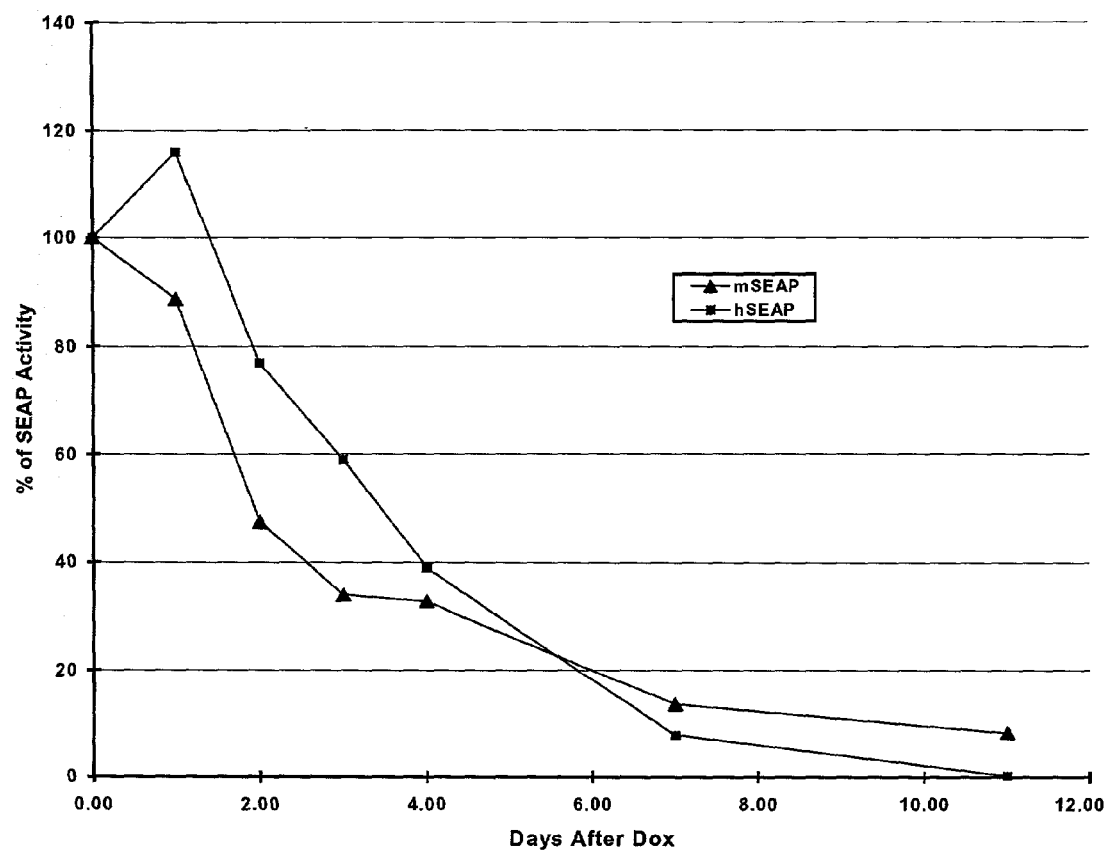
FIG. 5 demonstrates the comparable half-life of mSEAP and hSEAP in the bloodstream of Balb/C mice. Two plasmids were co-injected i.m., as per the method of Mir et al., PNAS 96:4262–7 (1999): 25 µg of a first plasmid encoding the transcription factor tTA, which is active in the absence of doxycycline; and 25 µg of a second plasmid encoding either the mSEAP (pMW19) or encoding the hSEAP. Both of the mSEAP and hSEAP sequences used are under the control of a tTA-responsive promoter. Alkaline phosphatase activity was assessed 7 days after gene transfer, after which mice were given doxycycline by gavage. Thereafter, the mice were given 0.2 mg/ml doxycyline in the drinking water. The triangles represent the percent of AP activity or protein present in the sample of blood following introduction of a mSEAP. The boxes represent the percent of AP activity or protein present in a sample following introduction of hSEAP. The half-life of AP activity or protein falls at nearly the same rate.

Furthermore, we have also demonstrated that the stable levels of mSEAP activity shown in FIG. 3 is not due to its stability in the bloodstream but rather to its sustained and persistent synthesis or expression by the cells bearing the transgene. In FIG. 5, we measure the decay of mSEAP and hSEAP activity after shutting down transcription. To accomplish this, we co-injected mice with two plasmids: one plasmid encoding the transcription factor tTA, which is active in the absence of doxycycline; and the second plasmid encoding mSEAP (pMW19) or hSEAP under the control of a tTA-responsive promoter (see, for example, Urlinger, et al., PNAS 97: 7963–68 (2000)). The mice are given doxycyline 7 days after gene transfer and the alkaline phosphatase activity assessed thereafter.

The results in FIG. 5 show that the half-life of mSEAP activity is less than 2 days and that the half-life of hSEAP activity is less than 4 days. These numbers take into account the half-life of the reporter protein, of its mRNA, and the decay of the transcription rate upon doxycycline administration. Hence, the sustained mSEAP activity shown in FIG. 3 cannot be explained by a prolonged half-life of mSEAP in the bloodstream.

Figure 6:
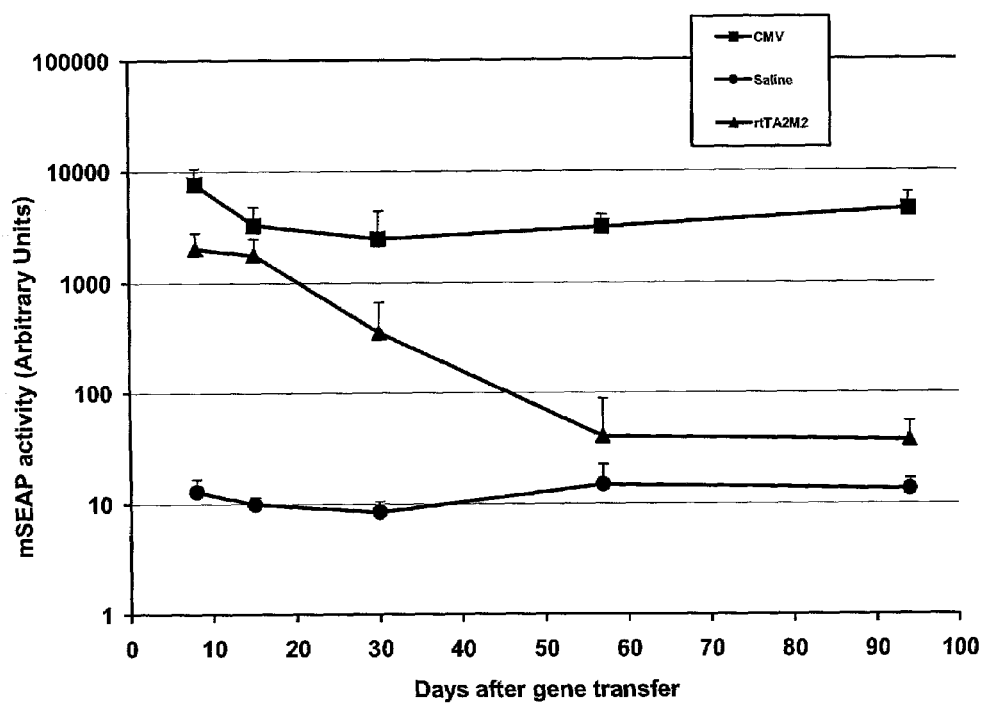
FIG. 6 shows the results of a method of analyzing long term expression in a mammal. Balb/C mice are injected i.m. with 25 μg plasmid DNA encoding mSEAP under the control of a CMV transcription promoter; or with 25 μg plasmid DNA encoding mSEAP under the control of rtTA2M2 in combination with 25 μg plasmid DNA encoding rtTA2M2; or with saline as control. See Urlinger et al., *PNAS* 97: 7963–68 (2000). Gene transfer was enhanced by electric pulses according to Mir et al. (1999), noted above. Mice were given 0.2 mg/ml doxycycline in the drinking water. The AP activity is assessed at the indicated time points. The boxes represent expression levels following introduction of an mSEAP under the control of the CMV promoter. The triangles represent the expression levels following introduction of an mSEAP under the control of the tTA-responsive promoter.

The utility of this invention is further demonstrated by the experiment presented in FIG. 6. We assessed the impact of the chimeric transcription factor rtTA2M2 (see, for example, Urlinger, et al., PNAS 97: 7963–68 (2000)) on the duration of mSEAP expression. In this experiment, mice are injected with a plasmid expressing mSEAP under the control of a constitutive transcription promoter (CMV) or with a plasmid expressing mSEAP under the control of an rtTA2M2-responsive promoter in combination with an rtTA2M2-encoding plasmid. Animals are given doxycycline (a water-soluble derivative of tetracycline) in the drinking water because rtTA2M2 is activated by this molecule. This experiment demonstrates clearly that rtTA2M2 is not capable of sustaining high levels of expression of mSEAP for more than 15 days. This may be due to a cytotoxic immune response against the cells expressing rtTA2M2 and mSEAP (rtTA2M2 is a fusion protein made of domains of bacterial and viral origins). In contrast, the CMV-driven expression of mSEAP results in stable levels of expression. Thus, the method of expressing a transgene or the method of analyzing long term expression of a transgene provided by this invention allows one to select appropriate regulatory elements and vectors for long term expression applications. Numerous regulatory elements exist in the art and can be selected for use and analysis. The invention is not limited to the use of any particular regulatory element or those specifically exemplified here.

The results discussed above and in the following specific examples are merely representative of the scope of the invention and content of this disclosure. One skilled in the art can use the information here to devise, produce, and use additional embodiments of the invention. Thus, the examples given here should not be taken as a limitation on the scope or extent of the invention.

EXAMPLE 1

Production of Plasmids Comprising AP Activity-encoding Nucleic Acids

A nucleic acid encoding the mSEAP reporter gene or polypeptide of the invention can be derived from mouse genomic DNA, synthesized from a GenBank sequence, or derived from one of the plasmids containing an EAP gene (for example, pSVT7-EAP from Narisawa et al., Development 116:159–165 (1992), Manes et al., Genomics 8: 541–554 (1990); or those of Hahnel et al., Development 110: 555–564 (1990); Bao et al., Gynocologic Oncology 78:373–379 (2000); Berger et al., Gene 66:1–10 (1988)), or derived from a mammalian AP gene or cDNA or other nucleic acid (for example, mouse secreted embryonic phosphatase—such as ACCESSION AY054302; mouse alkaline phosphatase 5—such as ACCESSION NM_00743; human intestinal alkaline phosphatase—such as ACCESSION M31008 M15184; human adult intestinal alkaline phosphatase—such as ACCESSION M15694; human intestinal alkaline phosphatase—such as ACCESSION NM_00631; rat membrane associate intestinal alkaline phosphatase—such as ACCESSION X17611 S51096; human alkaline phosphatase—such as ACCESSSION X55958; human placental alkaline phosphatase—such as ACCESSION M13077; rat intestinal alkaline phosphatase 1—such as ACCESSION NM_022665; human placental like alkaline phosphatase—such as ACCESSION X53279; human placental alkaline phosphatase type 1—such as ACCESSION M14169; pSEAP-Enhancer—ACCESSION U09662; pSEAP-Promoter—ACCESSION U09663; pSEAP2-Promoter—ACCESSION U89940; human clone MGC:5096 IMAGE:3460735—such as ACCESSION BC009647; pSEAP-Basic—such as ACCESSION U09660; bovine intestinal alkaline phosphatase III—such as ACCESSION AF052226; canine intestinal alkaline phosphatase—such as ACCESSION AF250845; feline alkaline phosphatase—such as ACCESSION U31569). From either the cloned gene sequence, the genomic sequence, the cDNA, or other nucleic acid, appropriate PCR oligos are prepared that result in the deletion of about 22 codons from those immediately preceding the stop codon. The determination of the number of codons to delete or truncate from the C-terminus depends on the functional properties of the resulting polypeptide. Functionally, the deletion of the C-terminal codons removes the membrane anchoring activity possessed by the native C-terminal amino acids. Accordingly, any C-terminal truncation resulting in a polypeptide that functionally lacks a membrane anchoring activity can be used and is included in this invention.

In one way of truncating the C-terminus, a stop codon is added or supplied at the desired end of the coding region. For example, a mouse genomic fragment encoding EAP can be amplified by PCR with oligonucleotides A and B below to generate the mSEAP of SEQ ID NO: 2. Alternatively, oligos A and C can be used to generate the full-length EAP encoding fragment. The full-length fragment can be used to create mutations or as a control.

```
                                           (SEQ ID NO:4)
A: 5'-GTATAAGCTTGCCACCATGTGGGGAGCCTGCTTGCTGCTGC-3'

(SEQ ID NO:5)
B: 5'-GTTTTCTAGATCAGCCCGGGCTCACTGCACTGCTCTGG-3'

(SEQ ID NO:6)
C: 5'-ACTCTCTAGATCAGGGTTCAGCCGCCGCCATCAGC-3'
```

Figure 2A:
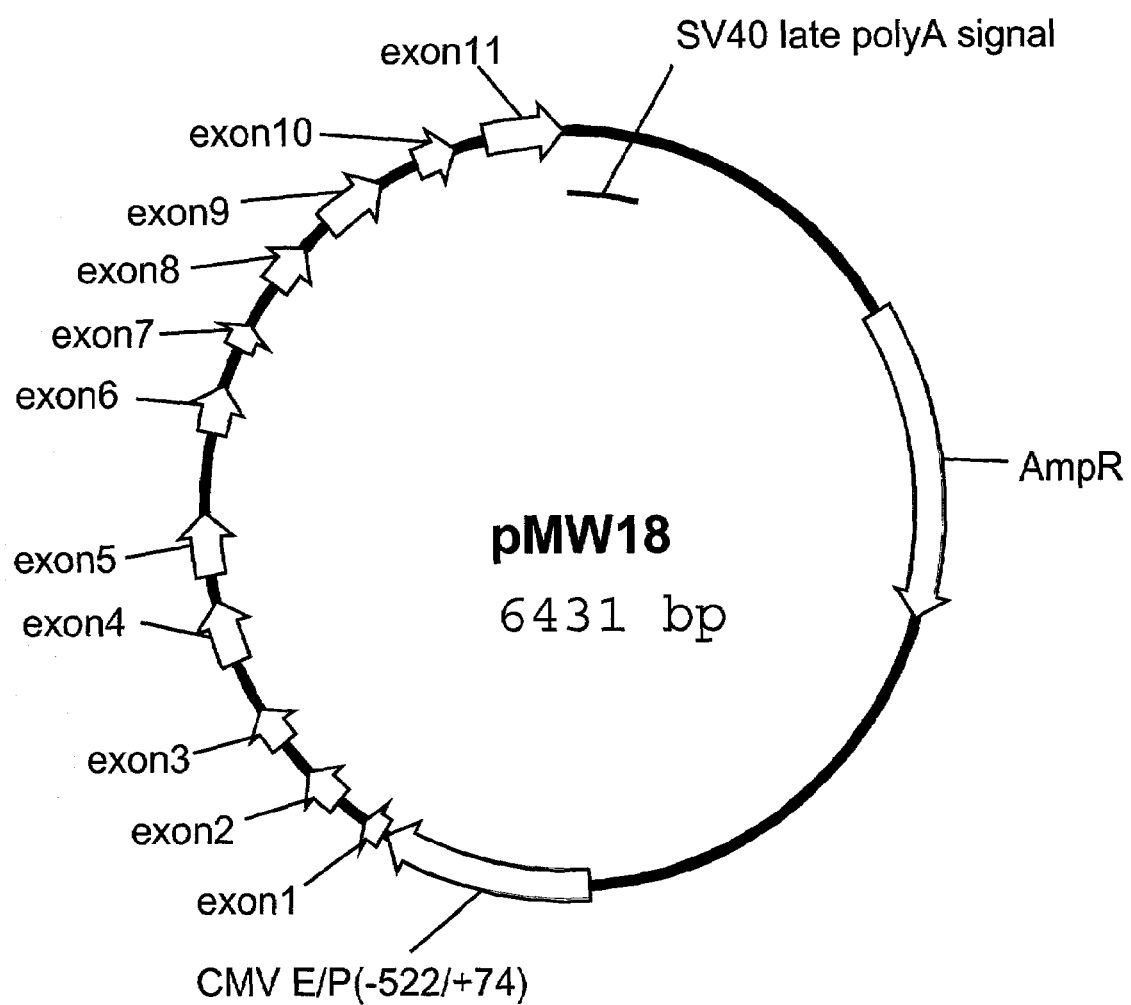
FIG. 2A is a plasmid map of pMW18, described in Example 1. It includes the C-terminal truncated form of the EAP coding region.
Figure 2B:
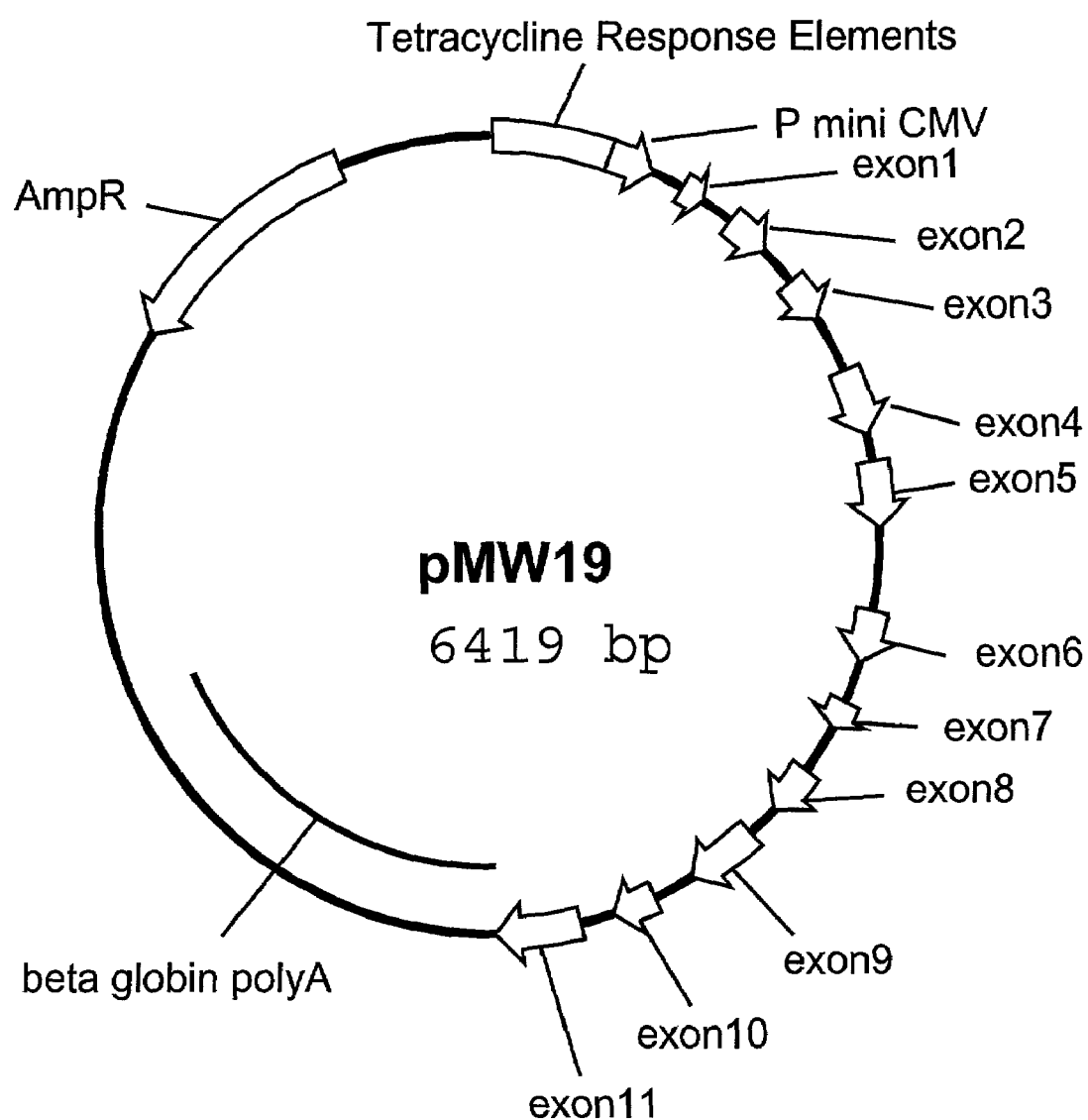
FIG. 2B is a plasmid map of pMW19, described in Example 1. It includes the C-terminal truncated form of the EAP coding region.

In one method, the PCR fragments are cut by HindIII and XbaI and inserted between the HindIII and AvrII sites of pXL3443 (a pBKSII-derived plasmid containing the CMV I/E promoter and the SV40 late poly(A) signal separated by a multiple cloning site) to generate pMW12 and pMW18 (see FIG. 2A). The same insert can be used between the HindIII and XbaI sites of pTRE2 (Clontech, Palo Alto, Calif.) to generate pMW19 (see FIG. 2B). Plasmid pMW12 harbors the native EAP gene and pMW18 the genomic clone with a truncation at the C-terminal end of the EAP coding region, both under the control of the CMV I/E promoter (from about −522 to about +74 from the start), and the SV40 late poly(A) signal. Plasmid pMW19 directs the transcription of the truncated murine EAP gene from a CMV I/E minimal promoter (from about −51 to about +70 from the start) under the control of a tetracycline response element (see, for example, Gossen and Bujard, PNAS 89: 5547–5551 (1992); (Urlinger, et al., PNAS 97: 7963–68 (2000)), with a β-globin poly(A) signal.

A cDNA encoding mSEAP of SEQ ID NO: 2 can be obtained as follows. Murine C2C12 myoblasts are transiently transfected with pMW 18 complexed to LipofectAMINE (Invitrogen—Life Technologies, Gaithersburg, Md.) according to the manufacturer's protocol. PolyA$^+$ RNA is extracted from transfected cells with a commercial kit (Dynal dynabeads mRNA direct kit). PolyA$^+$ RNA is reverse-transcribed and amplified by PCR (RT-PCR kit; Promega, Madison, Wis.) with oligonucleotides C9415 and C9416, shown below.

```
                                           (SEQ ID NO:7)
C9415: 5'-CGCGAAGCTTGCCACCATGTGGGGAGCCTGCTTGC-3'

(SEQ ID NO:8)
C9416: 5'-CTCTTCTAGACTATCAGCCCGGGCTCACTGCACTGC-3'
```

Figure 2C:
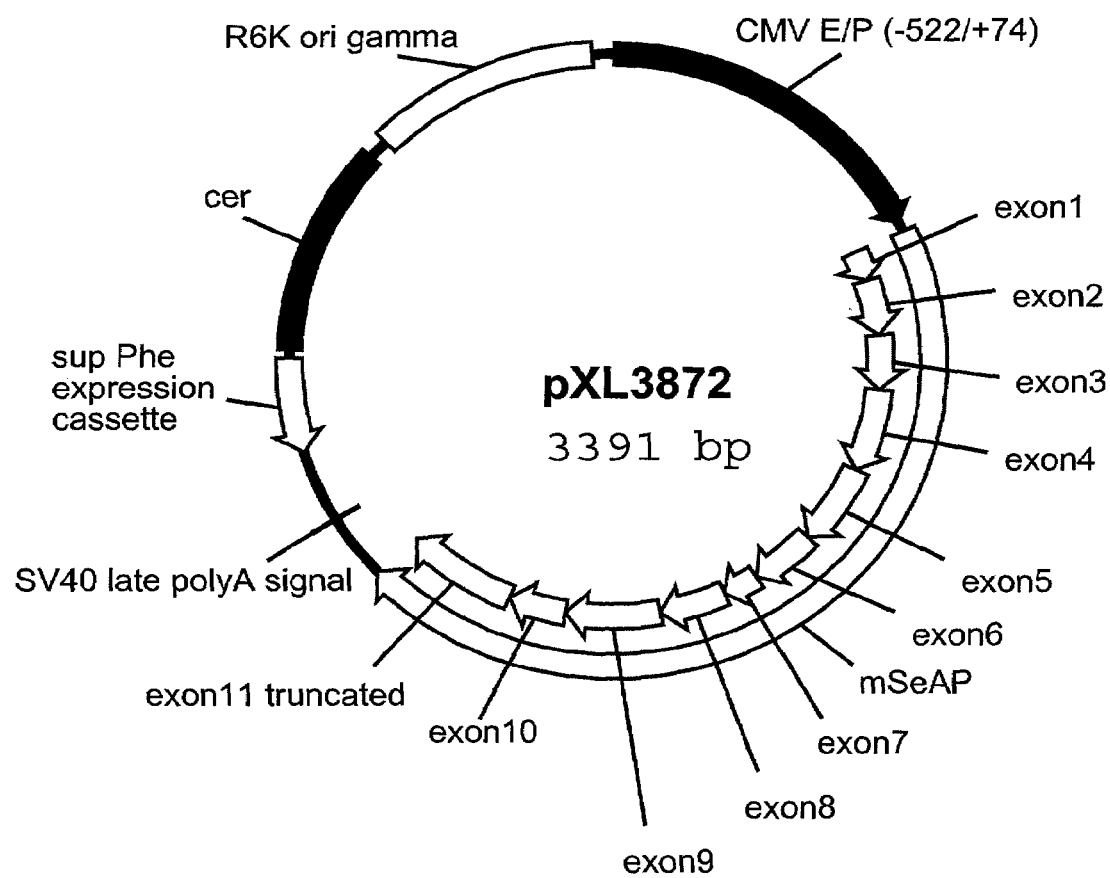
FIG. 2C is a plasmid map of pXL3872, described in Example 1. It includes the mSEAP cDNA. Exon 11 has been truncated as described in the examples (listed here as "exon 11 truncated").

Oligos C9415 and C9416 are designed to amplify the mSEAP nucleic acid flanked at the 5' end by a HindIII site, and flanked at the 3' end by an XbaI site. The product of the RT-PCR reaction is ligated in pGEMT-easy (Promega, Madison, Wis.) and transformed into E. coli DH5α. The resulting plasmid contains the mSEAP cDNA surrounded by a multiple cloning site. A plasmid pCOR (see Soubrier et al., Gene Therapy 6: 1482–88 (1999)) can then be used to construct a plasmid pXL3872 (FIG. 2C) containing the mSEAP nucleic acid under the control of the CMV I/E promoter (−522/+74) and the SV40 late poly(A) signal using the HindIII to XbaI sites of pXL3856 (a pCOR plasmid containing the CMV I/E promoter (−522/+74) and the SV40 late poly(A) signal). The expression cassette region of plasmid pXL3872 (FIG. 2C) is verified by sequencing.

Plasmids encoding other AP sequences are constructed in like manner for control AP proteins, for other mSEAP polypeptides of the invention, or derivative mSEAP polypeptides of the invention. For example, pXL3402 is a pCOR (Soubrier et al., 1999) plasmid with the SEAP cDNA under the control of the CMV I/E promoter (−522/+74) and the SV40 late poly(A) signal. Other plasmids put the SEAP under the control of the tetracycline responsive elements (TRE) and the SV40 late poly(A) signal. In another example, the PstI-SpeI fragment encoding luciferase in pBi-L (Baron et al., Nucleic Acids Res. 23:3605–06 (1995)) can be replaced by nucleic acid encoding an AP activity flanked by the PstI and SpeI sites. A PCR amplified fragment from pSEAP2-basic (Clontech) can be used. Also, a plasmid with an AP activity under the control of the CMV I/E promoter and the SV40 late poly(A) signal can be constructed by replacing the SacI-PvuII fragment of pBi-L (TRE) by the SacI-StuI fragment of pXL3031 (CMV IIE promoter, Soubrier et al., 1999) and subsequently replacing the luciferase ORF by the SEAP ORF.

The plasmids can be prepared for gene transfer administration by purification with the endo-free Mega-Prep kit (Qiagen, Germantown. Md.). Preferably, the endotoxin level detected in the samples is less than 20 EU per mg of DNA. Other methods and techniques for purifying vectors and nucleic acids for administration to a mammal are known in the art and can be used.

EXAMPLE 2

Transfection of Cultured Cells

C2C12 (ATCC: CRL1772), and HEK293 (ATCC: CRL1573) cells are seeded in 24-well plates ($7.5 \times 10^4$ cells per well) and grown for 24 h in DMEM supplemented with 10% FCS. Cells are then washed in DMEM without serum and transfected in triplicate by adding to the cells 0.5 ml of OptiMEM mixed with various quantities of AP-encoding plasmid, supplemented to 500 ng with a carrier plasmid and LipofectAMINE (2 µl for C2C12, 3 µl for HEK293). Five hours later, the medium containing the DNA and the LipofectAMINE is replaced by 1 ml of DMEM supplemented with FCS (2% for C2C12, 10% for HEK293). Aliquots of the culture medium are collected 2 days post-transfection and frozen at −70° C. for storage. The cells are rinsed twice with PBS, incubated with 100 µl of 0.2% Triton X-100, 50 mM Tris-HCl pH 7.4, 150 mM NaCl, detached from the plate with a scraper and homogenized by repeated pipetting. The lysate is centrifuged 2 minutes at maximum speed in an eppendorf tabletop centrifuge, and the supernatant stored at −70° C.

EXAMPLE 3

Intramuscular Gene Transfer

Eight-week-old female Balb/C or C57B1L6 mice (Charles River Laboratories, Wilmington, Mass.) are anesthetized by intraperitoneal injection of 200 µl ketamine (8.66 mg/ml) mixed with xylazine (0.31 mg/ml) in 150 mM NaCl. The hind legs are shaved. Twenty-five microliters of a nucleic acid vector containing solution in 150 mM NaCl are injected in the tibialis cranialis muscle. Thirty seconds after injection, transcutaneous electric pulses can be applied through stainless steel parallel electrodes connected to an Electro Square Porator, Model T820 (BTX, San Diego, Calif.), and a TDS 210 oscilloscope (Tektronix, Oreg.). If used, the plate electrodes are placed on each side of the leg (plate separation distance 4 mm) and 8 square wave pulses (80 volts, 20 ms each pulse, 1 pulse per second) are applied (Mir et al., 1999).

At different time points relative to DNA injection, 50 µl blood samples are collected from the saphenous vein into heparinized capillary tubes (Hem et al., Lab. Anim. 32:364-68 (1998)). Samples are spun 20 minutes at 2000 rpm in a clinical centrifuge and plasma collected and frozen at −70° C. for storage.

EXAMPLE 4

Reporter Gene Expression Analysis

Exemplary Enzymatic Assay

Detection of the AP activity can be carried out with the Phospha Light kit (Tropix, Perkin-Elmer), following the manufacturer's instructions or by using the modifications of Cullen and Malim, Meth. Enzymol. 216: 362–8 (1992)). Fifteen (15) µl of plasma or cell culture medium or cell extract are diluted into 45 µl of 1×dilution buffer (50 mM Tris-HCl pH 7.4; 150 mM NaCl), heated at 65° C. for 5 minutes, then cooled down to 4° C. in a PCR block thermocycler. Fifty (50) µl of diluted sample are incubated 5 minutes at room temperature with 50 µl of assay buffer (1M diethanolamine pH 10.5–11, 1 mM MgCl2, 10 mM L-homoarginine) before adding 50 µl of reaction buffer (CSPD substrate with Emerald enhancer). The reaction is then incubated 20 minutes at room temperature before chemiluminescence measurement (10 seconds per well) in a MLX microtiter plate luminometer (Dynex).

Exemplary ELISA Assay

Detection of antibodies directed against AP, for example the hSEAP in Table 1, can be performed using an ELISA assay. However, similar assays for other AP proteins, such as those of the invention, can also be used. Wells of a PVC microtiter plate are coated with 50 µl of a 0.5 µg/ml solution of human placental alkaline phosphatase (PLAP, Sigma) in 0.2 M Na$_2$CO$_3$/NaHCO$_3$ pH 9.5 and incubated overnight at 4° C. The plate is washed 3 times with 250 µl of 0.1 M phosphate buffer pH 7.5, 0.1 M NaCl (PBS), 0.05% Tween 20 (w/v). The remaining sites for protein binding on the PVC plate are saturated by incubation with PBS, 2% BSA (w/v) for 2 hours at room temperature. Fifty microliters of test plasma or positive or negative controls are added per well and incubated 2 hours at room temperature. The negative control can be the plasma of untreated Balb/c mouse. The positive control is obtained by spiking the plasma of a negative control mouse with 64 ng/ml of a mouse monoclonal antibody to PLAP (clone 8B6, Sigma Immunochemicals). Plasma samples are tested at dilutions 1:1 to 1:64 (two-fold serial dilutions in PBS). Samples are then incubated 1 hour at room temperature with a goat anti-rabbit IgG conjugated to horseradish peroxidase (Bio-Rad) in PBS, 2% BSA (w/v), 0.05% Tween 20, and washed 3 times with 250 µl of PBS, 0.05% Tween 20. The samples are reacted with 100 µl 3,3',5,5'-tetramethylbenzidine (USB, Ohio) for 15 minutes at room temperature, and the reaction stopped by adding 50 µl of 0.5 N H$_2$SO$_4$. The absorbance is read at 450 nm.

EXAMPLE 5

Long Term Expression Analysis

Mice are injected i.m. with 25 µg plasmid DNA encoding hSEAP, mSEAP of the invention, or saline control. Gene transfer is enhanced by electric pulses according to Mir, et al., PNAS 96:4262–7 (1999). Blood samples are collected in heparinized capillaries at the indicated time points by saphenous vein puncture, spun 20 minutes at 2000 rpm in a clinical centrifuge, and 12.5 µl of serum assessed for alkaline phosphatase activity according to the instructions in the phosphalight kit (Tropix), except that diluted plasma samples are heated 5 minutes at 65° C. Results for exemplary experiments of this type are shown in FIG. 3. The mSEAP levels, at the top of the chart, are detected in the first sample after gene transfer and remain consistently high throughout the entire sampling period (over 9 months). In contrast, the hSEAP reporter gene can be detected at levels above control for only about 20 days, and the levels vary greatly. The levels and relative errors reported indicate that the inventive mSEAP reporter genes can be used for extremely long expression studies and that the levels of expression are consistent and reproducible.

EXAMPLE 6

Preparation of mSEAP-encoding Nucleic Acids and Derivative Polypeptides; Analyzing Expression Vectors The nucleic acids derived from the mEAP gene noted in Example 1 can be used as the starting point to generate conservative amino acid substitution mutants and derivatives of the mSEAP proteins of the invention. The mSEAP encoding sequence is PCR amplified with an oligo that incorporates one or more nucleotide changes that result in amino acid substitutions. For example, the method described in Ausubel et al. Current Protocols in Molecular Biology (chapter 3 and unit 3.17, and chapter 8 and unit 8.5, in particular) can be adapted. The amino acid positions noted by the underlining in FIG. 7 represent exemplary sites for conservative amino acid changes or amino acid substitutions and the positions can be correlated to the sequence of any selected alkaline phosphatase activity-encoding nucleic acid used. For example, positions 358, 357, and/or 356 can be modified to encode an isoleucine in place of a valine, and/or a glutamic in place of an aspartic, and/or an arginine in place of a lysine. Once inserted into the sequence, the substitution mutant sequence can be incorporated into a plasmid as in Example 1. The mutant or derivative mSEAP protein can then be expressed as in Example 5 and tested to confirm long term expression and/or the ability to be used in immuno-competent mammals. Any derivative polypeptide possessing the long term expression characteristics noted above and throughout this disclosure is included in the invention. Testing for these characteristics can be performed as described here. Preferably, the derivative polypeptide will possess about 98%, or about 95%, or about 90%, or about 85%, or about 80%, or about 75% amino acid identity to SEQ ID NO: 1 or 2 in a blast comparison at default parameters.

Exemplary derivative polypeptides can be made using the same techniques used in Example 1 to generate mSEAP nucleic acids. The 3' primer "B", SEQ ID NO:5, encodes a stop codon resulting in a 22 amino acid truncation in the incorporated PCR amplified product with the A primer, SEQ ID NO:4.

Translated B primer (SEQ ID NO:5) 3'5' Frame 2

Q S S A V S P G Stop S R K (SEQ ID NO: 15)

Selecting a new 3' primer by sliding the stop codon further into the coding sequence results in amplified products that contain fewer codons. Thus, truncated products are produced from the SEAP or EAP cDNAs or genomic clones nucleotides that correspond to 27 amino acid truncations from the murine EAP gene noted in Manes et al., Genomics 8:541–554 (1990). Preferred truncations of about 22 to about 27 amino acids from the mEAP C-terminal end are made in this way. Other truncations are possible, as one of skill in the art appreciates. Furthermore, other deletions and/or substitutions, with or without the C-terminal truncation, can also be selected. The resulting, amplified DNA is then incorporated into a mammalian expression vector, administered to an immuno-competent mouse, and the long term expression characteristics of the AP-activity is tested by the chemiluminescent assay (Tropix; Bedford, Mass.), for example. Preferred expression vectors include viral vectors, such as adenovirus, adeno-associated virus, or retrovirus, or plasmid vectors. By testing the AP activity using particular expression vectors or regulatory sequences, an appropriate vector can be selected or optimized for transgene expression. Ligand-dependent regulatory sequences can also be tested for their ability to control expression over long periods of time (see, for example, Abruzzese, et al., Hum. Gene Ther. 10:1499–1507 (1999); Urlinger et al., *PNAS* 97: 7963–68 (200)), such as the 40 day, 60 day, 90 day, 120 day, 180 day, or 270 day periods possible through the use of the invention.

The invention described and exemplified above is not limited to the specific embodiments and examples presented here. One skilled in the art can use the techniques and knowledge available through the documents and references noted and specifically incorporated herein, or other documents or references, to make and use additional embodiments. Thus, the description above should not be taken as a limitation of the scope or content of this invention.

We claim:

1. An isolated nucleic acid sequence comprising a polynucleotide sequence encoding a mammalian alkaline phosphatase activity-possessing polypeptide wherein said polypeptide comprises the amino acid sequence of SEQ ID NO: 1 or SEQ ID NO: 2.

2. An expression vector comprising the nucleic acid of claim 1.

3. A viral vector comprising the nucleic acid of claim 1.

4. A plasmid vector comprising the nucleic acid of claim 1.

5. An isolated mammalian cell comprising a nucleic acid of claim 1.

6. An isolated mammalian cell comprising a vector of claim 2.

7. An isolated mammalian cell comprising a vector of claim 3.

8. An isolated mammalian cell comprising a vector of claim 4.

9. The cell of claim 5 that is a mouse cell.

10. The cell of claim 5 that is a human cell.

11. The cell of claim 5 that is a primate cell.

12. An isolated nucleic acid encoding a polypeptide comprising SEQ ID NO: 1 linked to a mammalian signal sequence.

13. The isolated nucleic acid of claim 12, wherein the mammalian signal sequence is selected from SEQ ID NO: 3, 9,10,11 or 12.

14. An isolated nucleic acid encoding an amino acid sequence consisting of SEQ ID NO: 1.

15. An isolated nucleic acid encoding an amino acid sequence consisting of SEQ ID NO: 2.

16. A plasmid comprising a promoter operably linked to a polynucleotide sequence encoding a polypeptide comprising SEQ ID NO: 1 or SEQ ID NO: 2.

17. The plasmid of claim 16, wherein the promoter is a CMV promoter.

18. The plasmid of claim 16, wherein the promoter is a constitutive promoter.

19. The plasmid of claim 16, wherein the promoter is an inducible promoter.

20. The plasmid of claim 19, wherein the promoter is a tTA-responsive promoter.

21. The plasmid of claim 16, wherein the plasmid is pXL3872.

* * * * *